US009675277B2

(12) United States Patent
Arai et al.

(10) Patent No.: US 9,675,277 B2
(45) Date of Patent: Jun. 13, 2017

(54) BREAST THICKNESS MEASUREMENT DEVICE AND BREAST THICKNESS MEASUREMENT METHOD

(71) Applicant: FUJIFILM Corporation, Tokyo (JP)

(72) Inventors: Takahisa Arai, Kanagawa-ken (JP); Tomoki Inoue, Kanagawa-ken (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 15/084,138

(22) Filed: Mar. 29, 2016

(65) Prior Publication Data

US 2016/0206229 A1 Jul. 21, 2016

Related U.S. Application Data

(63) Continuation of application No. PCT/JP2014/064610, filed on Jun. 2, 2014.

(30) Foreign Application Priority Data

Sep. 30, 2013 (JP) ................................. 2013-203536

(51) Int. Cl.
A61B 6/00 (2006.01)
A61B 5/107 (2006.01)
(Continued)

(52) U.S. Cl.
CPC ............ *A61B 5/1075* (2013.01); *A61B 6/025* (2013.01); *A61B 6/0414* (2013.01); *A61B 6/502* (2013.01);
(Continued)

(58) Field of Classification Search
CPC ..... A61B 6/025; A61B 6/0414; A61B 6/0492; A61B 6/5223; A61B 6/544; A61B 6/545; A61B 6/547; A61B 6/502
See application file for complete search history.

(56) References Cited

U.S. PATENT DOCUMENTS 5,335,257 A   8/1994 Stunberg
6,837,854 B2* 1/2005 Moore ................. A61B 8/0825
                                                    600/437
(Continued)

FOREIGN PATENT DOCUMENTS

JP    6-261896 A   9/1994
JP    2004-208752 A   7/2004
(Continued)

OTHER PUBLICATIONS

International Search Report for PCT/JP2014/064610 mailed on Aug. 12, 2014.
(Continued)

*Primary Examiner* — Thomas R Artman
(74) *Attorney, Agent, or Firm* — Birch, Stewart, Kolasch & Birch, LLP

(57) ABSTRACT

In this breast thickness measurement device and breast thickness measurement method, radiation is radiated from a plurality of different angles to a breast that is in a compressed state, a plurality of image data are generated by means of a radiation detector, and a plurality of tomographic images are generated by reconfiguring on the basis of each image datum after same has been generated. In each tomographic image, the thickness of the compressed breast is calculated on the basis of a tomographic image in which the focal point matches a first marker and a tomographic image in which the focal point matches a second marker.

12 Claims, 19 Drawing Sheets

(51) Int. Cl.
*A61B 6/02* (2006.01)
*A61B 6/04* (2006.01)
*A61B 90/00* (2016.01)

(52) U.S. Cl.
CPC ...... *A61B 90/39* (2016.02); *A61B 2090/3966* (2016.02)

(56) References Cited

U.S. PATENT DOCUMENTS

| | | | |
|---|---|---|---|
| 7,570,732 B2 * | 8/2009 | Stanton | A61B 6/02 378/7 |
| 7,940,885 B2 * | 5/2011 | Stanton | A61B 6/02 378/4 |
| 8,768,026 B2 * | 7/2014 | Ren | A61B 6/0414 382/131 |
| 9,532,752 B2 * | 1/2017 | Goossen | A61B 6/0414 |
| 2004/0101095 A1 | 5/2004 | Jing et al. | |
| 2004/0122313 A1 * | 6/2004 | Moore | A61B 8/0825 600/437 |
| 2004/0131145 A1 | 7/2004 | Ohara | |
| 2007/0242794 A1 * | 10/2007 | Stanton | A61B 6/02 378/5 |
| 2009/0022273 A1 | 1/2009 | Kashiwagi et al. | |
| 2009/0123052 A1 | 5/2009 | Ruth et al. | |
| 2009/0262887 A1 | 10/2009 | Iordache et al. | |
| 2009/0268865 A1 * | 10/2009 | Ren | A61B 6/0414 378/37 |
| 2009/0274272 A1 * | 11/2009 | Stanton | A61B 6/02 378/62 |
| 2012/0093285 A9 * | 4/2012 | Ren | A61B 6/0414 378/37 |
| 2014/0226786 A1 * | 8/2014 | Goossen | A61B 6/0414 378/37 |
| 2014/0301529 A1 * | 10/2014 | Ren | A61B 6/0414 378/37 |
| 2015/0265186 A1 * | 9/2015 | Kuwabara | A61B 5/1075 378/37 |
| 2016/0206229 A1 * | 7/2016 | Arai | A61B 5/1075 |

FOREIGN PATENT DOCUMENTS

| | | |
|---|---|---|
| JP | 2006-519625 | 8/2006 |
| JP | 2009-22536 A | 2/2009 |
| JP | 2010-005157 | 1/2010 |
| JP | 2010-183965 A | 8/2010 |
| JP | 2011-172713 A | 9/2011 |
| JP | 2011-250842 A | 12/2011 |
| JP | 2012-512669 A | 6/2012 |
| JP | 2012-231901 A | 11/2012 |

OTHER PUBLICATIONS

Written Opinion of the International Searching Authority for PCT/JP2014/064610 (PCT/ISA/237) mailed on Aug. 12, 2014.

* cited by examiner

BREAST THICKNESS MEASUREMENT DEVICE AND BREAST THICKNESS MEASUREMENT METHOD

CROSS-REFERENCE TO RELATED APPLICATIONS

This application is a Continuation of International Application No. PCT/JP2014/064610 filed on Jun. 2, 2014, which is based upon and claims the benefit of priority from Japanese Patent Application No. 2013-203536 filed on Sep. 30, 2013, the contents all of which are incorporated herein by reference.

TECHNICAL FIELD

The present invention relates to a breast thickness measuring device and a breast thickness measuring method for measuring the thickness of a breast of a subject that has been compressed by a support table and a compression plate.

BACKGROUND ART

Heretofore, for capturing a radiographic image of a breast of a subject using a radiographic image capturing apparatus, it has been customary to place the breast on a support table, displace a compression plate toward the support table to compress the breast, and thereafter, irradiate the breast with radiation emitted from a radiation source. Then, the radiation that has passed through the breast is converted into image data with a radiation detector.

In the above sequence, it is desirable to accurately grasp the thickness of the breast in the compressed state. In Japanese Laid-Open Patent Publication No. 6-261896, Japanese Laid-Open Patent Publication No. 2004-208752, and Japanese Laid-Open Patent Publication No. 2009-22536, it is disclosed that a position detecting sensor is provided on a proximal end portion of the compression plate, which is spaced from the chest wall of the subject, and the vertical position of the compression plate is detected by the position detecting sensor in order to measure the distance between the compression plate and the support table, i.e., to measure the thickness of the compressed breast.

SUMMARY OF INVENTION

Heretofore, as described above, for capturing a radiographic image of a breast, the breast is compressed at a distal end portion of the compression plate while at the same time the thickness of the breast is measured at a proximal end portion of the compression plate that is spaced from the chest wall (breast) of the subject. In order to acquire good image data, the radiological technician touches and spreads the breast, which has been placed on the support table, into a thin state, and then causes the compression plate to compress the breast. In the event that the compressed breast is of a distorted shape, the thickness of the breast undergoes local variations, which tend to increase measurement errors of the position detecting sensor, and hence it becomes difficult to suitably measure the thickness of the breast. Furthermore, since the thickness of the breast is measured at the proximal end portion of the compression plate, which is spaced from the compressed breast, measurement errors are likely to increase further.

The present invention has been made in order to solve the above problems. An object of the present invention is to provide a breast thickness measuring device and a breast thickness measuring method, which are capable of accurately grasping the thickness of a breast that is in a compressed state.

A breast thickness measuring device according to the present invention basically includes a support table on which a breast of a subject is placed, a compression plate that is displaced toward the support table in order to compress the breast, a radiation source configured to apply radiation from a plurality of different angles to the breast, which has been compressed, a radiation detector configured to generate a plurality of image data based on the radiation that has been transmitted through the breast, and a reconstruction processor configured to reconstruct the image data in order to generate a plurality of tomographic images.

In order to achieve the above object, the breast thickness measuring device according to the present invention further includes a first marker provided on the compression plate on a side of a chest wall of the subject, a second marker provided on the support table on the side of the chest wall of the subject, a marker detector configured to detect tomographic images that have captured the first marker and tomographic images that have captured the second marker, from among the tomographic images, a marker selector configured to select a tomographic image that is focused on the first marker from among the tomographic images that have captured the first marker, and selecting a tomographic image that is focused on the second marker from among the tomographic images that have captured the second marker, and a thickness calculator configured to calculate the thickness of the breast, which has been compressed, based on the tomographic image that is focused on the first marker and the tomographic image that is focused on the second marker.

In order to achieve the above object, a breast thickness measuring method according to the present invention includes the following first through sixth steps.

In a first step, a compression plate with a first marker provided thereon on the side of a chest wall of a subject is displaced toward a support table with a second marker provided thereon on the side of the chest wall of the subject, for thereby compressing a breast of the subject that has been placed on the support table. In a second step, a radiation source applies radiation from a plurality of different angles to the breast, which has been compressed, and a radiation detector generates a plurality of image data based on the radiation that has been transmitted through the breast. In a third step, a reconstruction processor reconstructs the image data in order to generate a plurality of tomographic images. In a fourth step, a marker detector detects tomographic images that have captured the first marker and tomographic images that have captured the second marker, from among the tomographic images. In a fifth step, a marker selector selects a tomographic image that is focused on the first marker from among the tomographic images that have captured the first marker, and selects a tomographic image that is focused on the second marker from among the tomographic images that have captured the second marker. In a sixth step, a thickness calculator calculates a thickness of the breast, which has been compressed, based on the tomographic image that is focused on the first marker and the tomographic image that is focused on the second marker.

According to the present invention, there is performed a tomosynthesis image capturing process for applying radiation from a plurality of different angles to a breast in the compressed state, and a plurality of tomographic images are generated by reconstructing image data obtained by the tomosynthesis image capturing process. The first marker is provided on the compression plate, whereas the second marker is provided on the support table. Therefore, the tomographic image that is focused on the first marker is a tomographic image of an upper end of the breast along the thickness-wise direction of the breast. The tomographic image that is focused on the second marker is a tomographic image of a lower end of the breast along the thickness-wise direction. Consequently, using the tomographic image that is focused on the first marker and the tomographic image that is focused on the second marker, it is possible to directly calculate the thickness of the breast in the compressed state.

In addition, the first marker and the second marker are disposed on the side of the chest wall of the subject. Therefore, the present invention allows the compressed thickness to be calculated more accurately than with the technologies disclosed in the publications referred to above.

Therefore, according to the present invention, it is possible to accurately grasp the compressed thickness of the breast.

The tomographic images represent images at discrete cross sections spaced at predetermined slice intervals. Consequently, depending on the slice intervals or the slicing method, it is conceivable that a tomographic image may not necessarily be obtained at the vertical position of the first marker or the second marker. According to the present invention, a tomographic image in which the first marker is clearly visible is selected as the tomographic image that is focused on the first marker, from among the tomographic images that have captured the first marker. Similarly, a tomographic image in which the second marker is clearly visible is selected as the tomographic image that is focused on the second marker, from among the tomographic images that have captured the second marker. By selecting the tomographic image of the first marker and the tomographic image of the second marker in this manner, the accuracy in calculating the thickness of the breast is prevented from becoming lowered on account of the slice intervals and the slicing method.

The thickness calculator may calculate the thickness of the breast based on slice intervals of the tomographic images and the number of tomographic images from the tomographic image that is focused on the first marker to the tomographic image that is focused on the second marker. Therefore, the thickness calculator can reliably calculate the actual thickness of the breast.

The slice intervals are pre-adjusted using a commercially available calibration phantom (geometric calibration phantom), not shown, and are stored in a memory provided in the breast thickness measuring device, for example.

The reconstruction processor may reconstruct the image data to generate tomographic images such that the tomographic images are tomographic images sliced parallel to the support table. In this manner, it is easy to detect the tomographic images that have captured the first marker or the second marker.

The first marker and the second marker may be disposed in the manner indicated by items [1] through [3] below.

[1] The first marker and the second marker preferably are disposed in superposed relation as viewed as a planar view. Therefore, the burden imposed by a correcting process for generating a two-dimensional image from the tomographic images is reduced.

The radiation source preferably is supported for angular movement about a rotational shaft, and is angularly movable through a predetermined angle about a vertical axis perpendicular to the rotational shaft. The support table, the compression plate, and the radiation detector preferably are disposed on the vertical axis, and the first marker and the second marker preferably are disposed such that the vertical axis extends through the first marker and the second marker.

[2] The first marker preferably is disposed at one corner and another corner, along the chest wall, of the compression plate on the side of the chest wall. More specifically, as long as the first marker is disposed on left and right corners (one corner and another corner) of the compression plate on the side of the chest wall as viewed from the perspective of the subject, then even in a case that the compression plate compresses the breast while being tilted with respect to the support table, it is possible to calculate the thickness of the breast in the compressed state based on the average of the vertical positions of the two first markers.

[3] In [2] above, the first marker preferably is further disposed in a central area of the compression plate on the side of the chest wall. Therefore, based on the vertical positions of the three first markers, it is possible to grasp whether or not the compression plate has become distorted.

According to the present invention, the breast thickness measuring device may further comprise a two-dimensional image generator that generates a two-dimensional image of the breast by performing an addition process on the tomographic images. However, in the event that a simple addition process is performed on all of the tomographic images in order to generate a two-dimensional image of the breast from the tomographic images, then a two-dimensional image is generated in which the first marker and the second marker is captured. In this case, in a case where a doctor interprets and diagnoses the two-dimensional image which has been generated in this manner, the doctor may mistake the first marker and the second marker for a calcified region, spicula, mass, or the like, which is formed in the breast, and thus there is a possibility that the burden on the doctor could increase.

According to the present invention, as indicated in paragraphs (1) through (3) below, the two-dimensional image generator performs a predetermined correcting process for excluding the first marker and the second marker, to thereby generate a two-dimensional image.

(1) The two-dimensional image generator simply adds tomographic images, which have not captured the first marker or the second marker from among the tomographic images, in order to generate the two-dimensional image.

(2) The two-dimensional image generator performs a first addition process for simply adding tomographic images for image areas in which the first marker or the second marker does not exist, from among the tomographic images, performs a second addition process for simply adding, for image areas in which the first marker or the second marker exists, tomographic images from which the tomographic images that have captured the first marker or the second marker are excluded, from among the tomographic images, and combines two new images obtained by the first addition process and the second addition process, thereby generating the two-dimensional image.

(3) The two-dimensional image generator performs a correcting process for removing the first marker or the second marker on tomographic images in which the first marker or the second marker has been captured, from among the tomographic images, and simply adds tomographic images that have not captured the first marker or the second marker and the tomographic images on which the correcting process has been performed, thereby generating the two-dimensional image.

The breast thickness measuring device may further comprise an average glandular dose calculator that calculates an average glandular dose based on the thickness of the breast, which has been calculated by the thickness calculator. In this manner, it is possible to grasp an accurate radiation dose to which the breast is exposed. Consequently, provided that the thickness of the breast in the compressed state is calculated accurately from the tomographic images obtained by the tomosynthesis image capturing process, and provided that the average glandular dose is calculated accurately based on the calculated thickness of the breast, then in a case where a normal image capturing process is carried out on the breast after the tomosynthesis image capturing process, it is possible to accurately calculate a dose of radiation that is required to be applied in the normal image capturing process, based on the average glandular dose.

DESCRIPTION OF EMBODIMENTS

Figure 1:
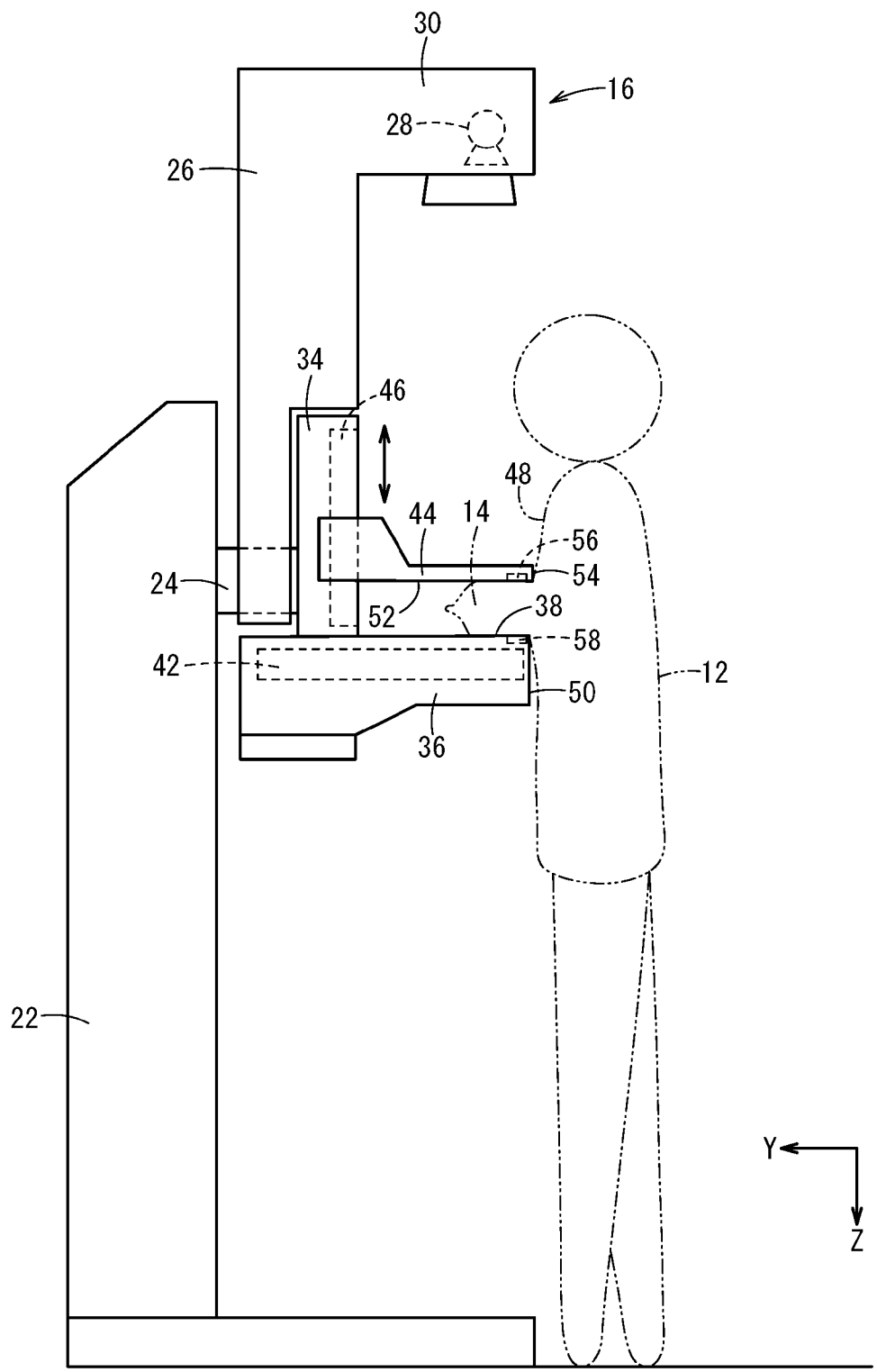
FIG. 1 is a side elevational view of a radiographic image capturing apparatus to which a breast thickness measuring device according to an embodiment of the present invention is applied.

Breast thickness measuring devices according to preferred embodiments of the present invention in relation to a breast thickness measuring method will be described in detail below with reference to the accompanying drawings.
[Arrangement of Breast Thickness Measuring Device]

As shown in FIGS. 1 through 4, a breast thickness measuring device 10 according to an embodiment of the present invention is applied to a radiographic image capturing system 20, which comprises a radiographic image capturing apparatus 16 for capturing a radiographic image of a breast 14 of a subject 12, and a console 18 for controlling the radiographic image capturing apparatus 16, in a radiological department of a medical organization.

Figure 2:
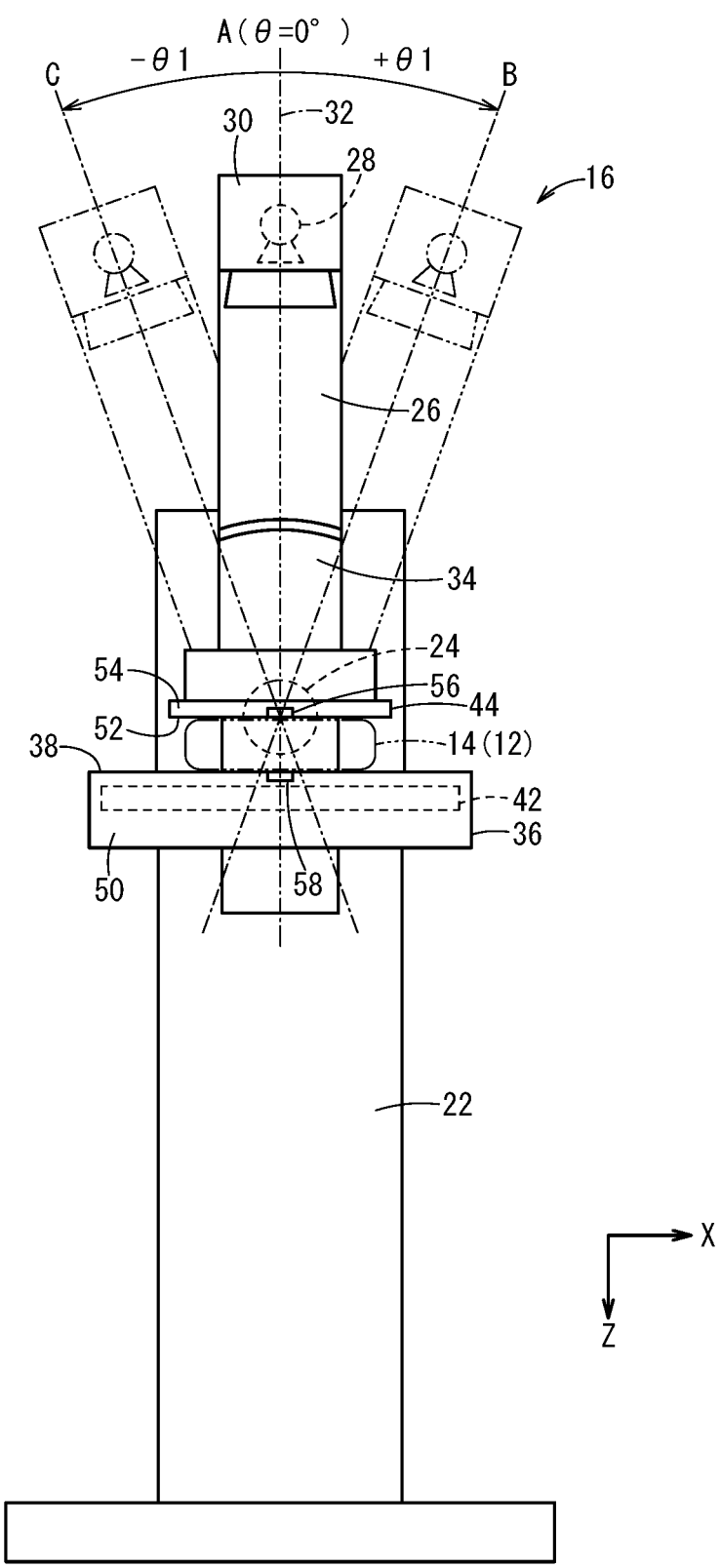
FIG. 2 is a front elevational view of the radiographic image capturing apparatus shown in FIG. 1.

As shown in FIGS. 1 and 2, the radiographic image capturing apparatus 16 includes an upstanding base 22 and a rotational shaft 24 that extends in the direction of the arrow Y as a horizontal direction from an upper portion of a side surface of the base 22 which faces toward the subject 12. An arm 26 is fixed to the rotational shaft 24.

The arm 26, which is supported on the rotational shaft 24, includes a distal end portion constructed as a radiation source housing 30 that houses a radiation source 28 therein. A vertical axis 32 extends perpendicularly to the rotational shaft 24 in a vertical direction (the direction of the arrow Z). Upon rotation of the rotational shaft 24 about its own axis, the arm 26, the radiation source 28, and the radiation source housing 30 rotate together within a predetermined angular range ($-\theta 1$ to $+\theta 1$) with the vertical axis 32 being located at a central angle ($\theta=0°$). In the description that follows, the position of the radiation source 28 at $\theta=0°$ will be referred to as position A, the position of the radiation source 28 at $\theta=+\theta 1°$ will be referred to as position B, and the position of the radiation source 28 at $\theta=-\theta 1°$ will be referred to as position C.

A holder 34 is coupled to the distal end of the rotational shaft 24. An image capturing table (support table) 36 on which the breast 14 of the subject 12 is placed is mounted on a lower end of the holder 34. At least a portion of the image capturing table 36 on the side of a placement surface 38 on which the breast 14 is placed is made of a material permeable to radiation 40 (see FIG. 4). The image capturing table 36 houses therein a radiation detector 42, which generates a radiographic image (an example of image data) based on radiation 40 that is emitted from the radiation source 28.

A compression plate 44, which is made of a material permeable to radiation 40, is mounted on the holder 34. The compression plate 44 is displaceable along the direction of the arrow Z by a compression plate moving mechanism 46 such as a rail or the like that is disposed in the holder 34. The holder 34, the image capturing table 36, the radiation detector 42, and the compression plate 44 are disposed bilaterally and symmetrically along the direction of the arrow X with respect to the vertical axis 32.

In a case where the compression plate 44 is lowered toward the image capturing table 36 by the compression plate moving mechanism 46, with a chest wall 48 of the subject 12 being held in contact with a side surface 50 of the image capturing table 36 on the side of the subject 12, and also with the breast 14 being placed on the placement surface 38, it is possible to compress the breast 14 between the placement surface 38 of the image capturing table 36 and a compression surface 52 defined by the bottom surface of the compression plate 44.

Respective gears, not shown, are provided on the rotational shaft 24 and the holder 34. By adjusting the intermeshing state of the gears, it is possible to switch between a state in which the holder 34 is coupled to the rotational shaft 24 for rotation therewith, and a state in which the holder 34 is separated from the rotational shaft 24 for idle rotation. Hereinbelow, a description will be given in which the placement surface 38 of the image capturing table 36 lies along the horizontal direction (the direction of the arrow X and the direction of the arrow Y) in a case where the holder 34 is rotatable in an idle state with respect to the rotational shaft 24.

According to the present embodiment, a first marker 56 is provided on the compression plate 44 proximate a side surface 54 thereof on the side of the chest wall 48 of the subject 12, and a second marker 58 is provided on the image capturing table 36 proximate a side surface 50 thereof on the side of the chest wall 48.

More specifically, the first marker 56 is embedded in the compression plate 44 so as to lie substantially flush with the compression surface 52 proximate the side surface 54, at a position on a central line 60 that is perpendicular to the vertical axis 32 and coaxial with the rotational shaft 24, i.e., at a central position proximate the side surface 54. The second marker 58 is embedded in the image capturing table 36 so as to lie substantially flush with the placement surface 38 proximate the side surface 50, at a position through which the vertical axis 32 and the central line 60 extend, i.e., at a central position proximate the side surface 50.

Figure 3:
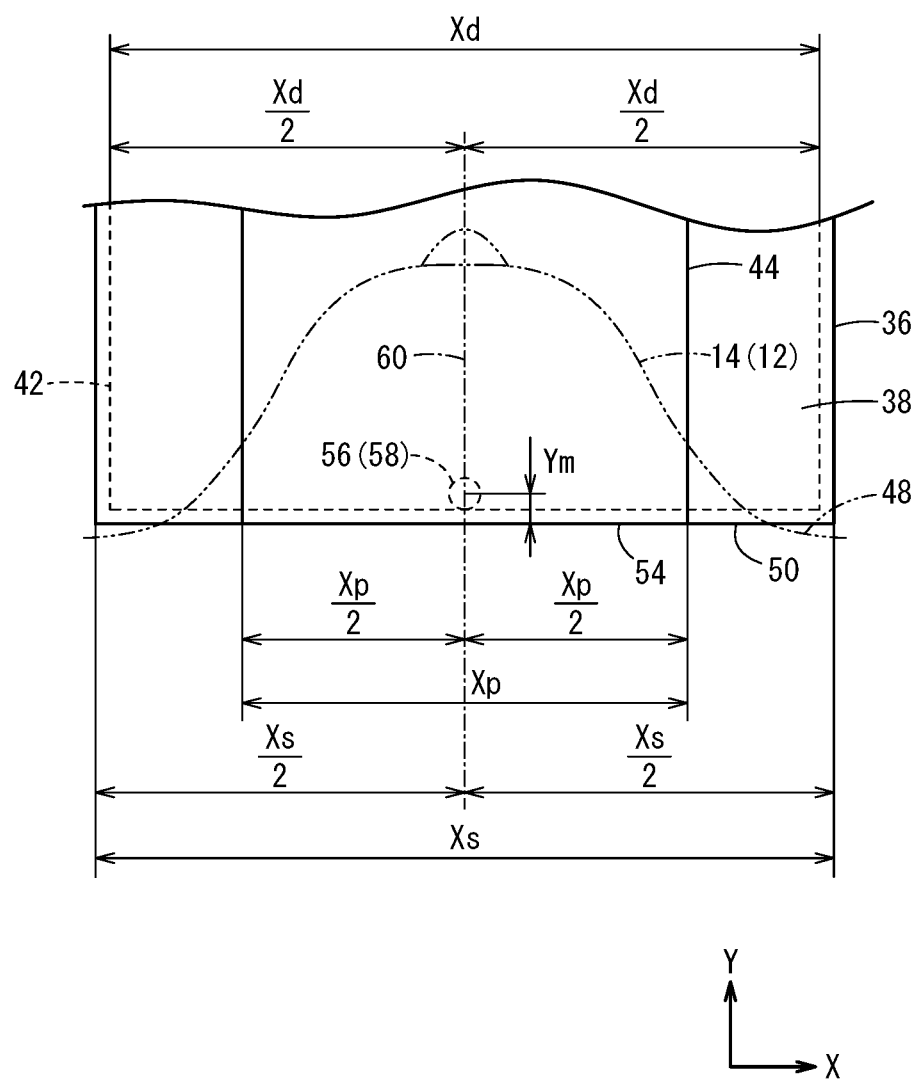
FIG. 3 is a planar view illustrating chest-wall sides of a compression plate and an image capturing table.

As shown in FIG. 3, given that the horizontal width of the image capturing table 36 along the direction of the arrow X is represented by Xs, the horizontal width of the radiation detector 42 is represented by Xd, and the horizontal width of the compression plate 44 is represented by Xp, the first marker 56 and the second marker 58 are located on the central line 60, which is a central position with respect to the direction of the arrow X of the image capturing table 36, the radiation detector 42, and the compression plate 44. Further, the first marker 56 and the second marker 58 are superposed one on the other, at a position that is spaced Ym back from the side surfaces 50, 54 in the direction of the rotational shaft 24 as viewed as a planar view.

Since the position that is spaced Ym back from the side surfaces 50, 54 is a position on the radiation detector 42 as viewed as a planar view, the first marker 56 and the second marker 58 are disposed within the irradiation range of the radiation 40. The first marker 56 and the second marker 58 are provided within the irradiation range of the radiation 40 and in the vicinity of the side surfaces 50, 54, such that Ym is allowed to be a distance that does not approach the central area of the compression plate 44 (e.g., only about few mm from the side surfaces 50, 54).

Since the image capturing table 36 is harder (of greater mechanical strength) than the compression plate 44, the second marker 58 may be provided in an arbitrary location proximate the side surface 50. In FIGS. 2 and 3, by way of example, the second marker 58 is illustrated as being disposed at a position through which the vertical axis 32 and the central line 60 extend.

The first marker 56 and the second marker 58 preferably are made of a material that is capable of absorbing radiation 40 (i.e., a material that is impermeable to radiation 40), such as copper, lead, platinum, gold, tantalum alloy, alumina, or the like. The first marker 56 and the second marker 58 may be of a shape that can be distinguished from a calcified region, spicula, mass, or the like, which may be formed in the breast 14. For example, the first marker 56 and the second marker 58 may be of a circular shape, a ring shape, a crisscross shape, or a heart shape as viewed as a planar view.

Figure 4:
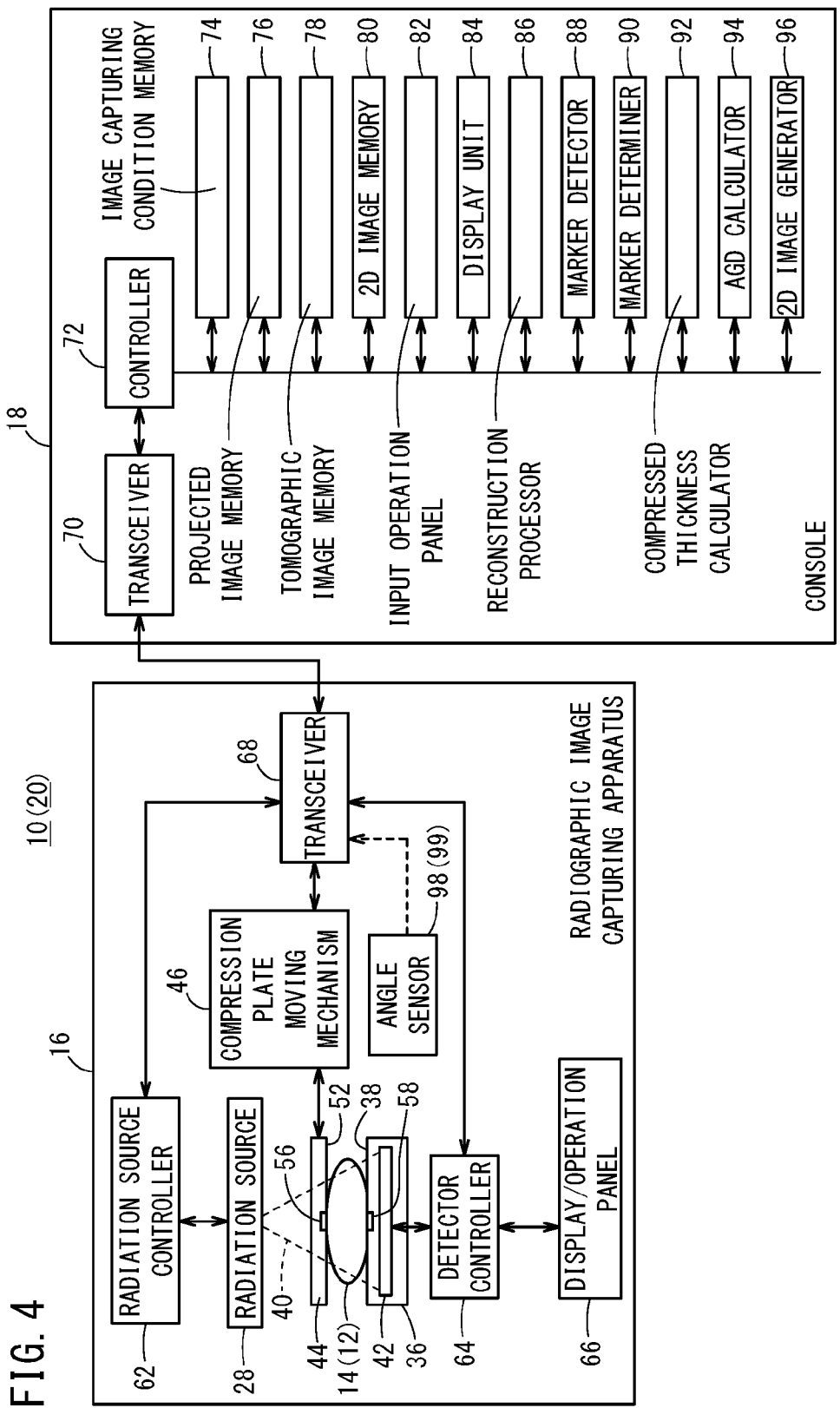
FIG. 4 is a block diagram of the breast thickness measuring device according to the embodiment.

As shown in FIG. 4, the radiographic image capturing system 20 to which the breast thickness measuring device 10 according to the present embodiment is applied comprises the radiographic image capturing apparatus 16 and the console 18.

The radiographic image capturing apparatus 16 includes, in addition to the components shown in FIGS. 1 through 3, a radiation source controller 62, a detector controller 64, a display control panel 66, and a transceiver 68. The radiation source controller 62 controls the radiation source 28 according to image capturing conditions transmitted from the console 18 through the transceiver 68. The detector controller 64 controls the radiation detector 42 according to the image capturing conditions in order to acquire a radiographic image that is generated by the radiation detector 42, and transmits the acquired radiographic image to the console 18 through the transceiver 68. The display control panel 66 displays image capturing information, such as an imaged region, an imaging direction, etc. of the subject 12, ID information of the subject 12, etc., and allows setting of such items, as necessary. The transceiver 68 sends signals to and receives signals from the console 18.

The image capturing conditions refer to conditions representing a tube voltage, an mAs value, etc., which define the dose of radiation 40 that is applied to the breast 14. In order to perform a radiographic image capturing process on the breast 14, such image capturing conditions are set in the radiation source controller 62.

The console 18 is installed in a treatment room adjacent to an image capturing room of the radiological department and controls the radiographic image capturing apparatus 16. The console 18 is connected to a hospital information system (HIS) for managing medical clerical work in the hospital, a radiological information system (RIS) for managing a process of capturing radiographic images in the radiological department under the management of the HIS, and a viewer that is used by the doctor in order to interpret and diagnose radiographic images.

More specifically, the console 18 includes a transceiver 70 for sending signals to and receiving signals from the radiographic image capturing apparatus 16, as well as sending signals to and receiving signals from the viewer, the HIS, and the RIS through an in-hospital network, and a controller 72 for controlling various components of the radiographic image capturing apparatus 16 and the console 18. In the console 18, an image capturing condition memory 74, a projected image memory 76, a tomographic image memory 78, a 2D image memory 80, an input operation panel 82, a display unit 84, a reconstruction processor 86, a marker detector 88, a marker determiner (selector) 90, a compressed thickness calculator (thickness calculator) 92, an AGD calculator (average glandular dose calculator) 94, and a 2D image generator (two-dimensional image generator) 96 are connected to the controller 72.

The image capturing condition memory 74 stores therein image capturing conditions, which have been set by the radiological technician operating the input operation panel 82. For performing a radiographic image capturing process on the breast 14, the controller 72 is capable of setting the image capturing conditions in the radiation source controller 62 through the transceivers 68, 70.

The projected image memory 76 stores a radiographic image acquired from the radiographic image capturing apparatus 16. More specifically, in a tomosynthesis image capturing process, which is performed on the breast 14 by the radiographic image capturing system 20, in a case where image capturing conditions depending on the tomosynthesis image capturing process are set in the radiation source controller 62, the radiation source controller 62 rotates the rotational shaft 24 according to the image capturing conditions, so as to turn the arm 26 within the angular range from −θ1 to +θ1 (i.e., a range between position B and position C) (see FIGS. 1 and 2).

At this time, the radiation source controller 62 controls the radiation source 28 to apply radiation 40 to the breast 14, which has been compressed by the image capturing table 36 and the compression plate 44, successively from positions at a plurality of different angles θ within the above angular range. Each time that radiation 40, which has passed through the breast 14, is projected onto the radiation detector 42, the radiation detector 42 converts the projected radiation 40 into a radiographic image. The detector controller 64 controls the radiation detector 42 in order to acquire the converted radiographic image. Therefore, the detector controller 64 is capable of acquiring from the radiation detector 42 a plurality of radiographic images in the tomosynthesis image capturing process that is performed on the breast 14. The acquired radiographic images are transmitted from the detector controller 64 to the console 18 through the transceivers 68, 70.

The projected image memory 76 stores the radiographic images that are represented by image data generated in a case where radiation 40 passes through the breast 14 and is projected onto the radiation detector 42 at respective different angles θ. Since the first marker 56 and the second marker 58, which are capable of absorbing radiation 40, are positioned within the irradiation range of the radiation 40, each of the radiographic images is represented by image data in which the first marker 56 and the second marker 58 are captured. The projected image memory 76 also stores various items of information assigned to the radiographic images, such as numbers, file names, headers, or the like, together with the radiographic images.

The reconstruction processor 86 reads the radiographic images that are stored in the projected image memory 76, and generates tomographic images (reconstructed images) of the breast 14 at arbitrary sectional positions (slice height) along the direction of the arrow Z, by applying a known image reconstructing process such as FBP (Filtered Back Projection) to each of the radiographic images that have been read. The tomographic images, which are generated by the reconstruction processor 86, are reconstructed images sliced parallel to the placement surface 38 of the image capturing table 36. Each of the reconstructed tomographic images is stored in the tomographic image memory 78. The tomographic image memory 78 also stores various items of information assigned to the tomographic images, such as numbers, file names, headers, or the like, together with the tomographic images.

The marker detector 88 detects, from among the tomographic images that are stored in the tomographic image memory 78, tomographic images that have captured the first marker 56 and tomographic images that have captured the second marker 58. The marker determiner 90 selects, from among the tomographic images detected by the marker detector 88, a tomographic image that is focused on the first marker 56, and a tomographic image that is focused on the second marker 58.

The tomographic images represent images at discrete cross sections, which are spaced at predetermined slice intervals. Consequently, depending on the slice intervals or the slicing method, it is conceivable that a tomographic image at the vertical position of the first marker 56 or at the vertical position of the second marker 58 may not necessarily be obtained. Therefore, the marker determiner 90 selects, from among the tomographic images that have captured the first marker 56, the tomographic image in which the first marker 56 is most clearly visible as the tomographic image that is focused on the first marker 56. The marker determiner 90 also selects, from among the tomographic images that have captured the second marker 58, the tomographic image in which the second marker 58 is most clearly visible as the tomographic image that is focused on the second marker 58.

In addition to the tomographic images themselves, the tomographic image memory 78 stores various items of information concerning the tomographic images. Therefore, during the process of detecting tomographic images, which is carried out by the marker detector 88, and the process of selecting tomographic images, which is carried out by the marker determiner 90, various processes may be performed using various items of information that are assigned to the tomographic images.

More specifically, from among the various items of information assigned to the tomographic images, the marker detector 88 may specify various items of information assigned to the tomographic images that have captured the first marker 56 and the tomographic images that have captured the second marker 58, to thereby enable detection of the tomographic images that have captured the first marker 56 and the tomographic images that have captured the second marker 58.

The marker determiner 90 may specify various items of information assigned to the tomographic image that is focused on the first marker 56 and the tomographic image that is focused on the second marker 58, from among various items of information assigned to the tomographic images that have captured the first marker 56 and the tomographic images that have captured the second marker 58, thereby selecting a tomographic image that is focused on the first marker 56 and a tomographic image that is focused on the second marker 58.

Therefore, the process of detecting tomographic images, which is carried out by the marker detector 88, and the process of selecting tomographic images, which is carried out by the marker determiner 90, include various processes with respect to various items of information assigned to the tomographic images.

The compressed thickness calculator 92 calculates the thickness of the breast 14 in a compressed state (compressed thickness), using the tomographic image that is focused on the first marker 56 and the tomographic image that is focused on the second marker 58, which have been selected by the marker determiner 90. More specifically, the tomographic image that is focused on the first marker 56 and the tomographic image that is focused on the second marker 58 can be regarded as tomographic images sliced at vertical positions of the first marker 56 and the second marker 58. Consequently, the compressed thickness calculator 92 calculates the compressed thickness on the basis of the two tomographic images, depending on the vertical positions of the first marker 56 and the second marker 58.

The compressed thickness calculator 92 may calculate the compressed thickness using various items of information assigned to the tomographic image that is focused on the first marker 56, and the tomographic image that is focused on the second marker 58. Therefore, the calculating process carried out by the compressed thickness calculator 92 covers the concept of calculating the compressed thickness using various items of information assigned to the tomographic images.

The AGD calculator 94 calculates an average glandular dose (AGD) of the breast 14, on the basis of the compressed thickness calculated by the compressed thickness calculator 92. The 2D image generator 96 performs a predetermined addition process on the tomographic images that are stored in the tomographic image memory 78, thereby generating a 2D image (two-dimensional image) that is displayed on the viewer for the doctor to interpret and diagnose the radiographic images. The generated 2D image is stored in 2D image memory 80.

The display unit 84 displays the image capturing conditions, which are stored in the image capturing condition memory 74, the radiographic images and the various items of information assigned thereto, which are stored in the projected image memory 76, and the tomographic images and the various items of information assigned thereto, which are stored in the tomographic image memory 78. The display unit 84 also displays the 2D image stored in the 2D image memory 80, the compressed thickness calculated by the compressed thickness calculator 92, and/or the AGD calculated by the AGD calculator 94.

The 2D image memory 80, the AGD calculator 94, and the 2D image generator 96 are included in the console 18 only as necessary, and are not considered indispensable components. The radiographic image capturing apparatus 16 may include angle sensors 98, 99 that detect a tilt angle of the compression plate 44 with respect to the direction of the arrow X or the direction of the arrow Y (horizontal plane). Similarly, the angle sensors 98, 99 are included in the radiographic image capturing apparatus 16 only as necessary, and are not considered indispensable components.

The image data will be described in greater detail below. As has been described above, the radiation detector 42 generates radiographic images as an example of image data, the detector controller 64 reads the radiographic images and transmits the radiographic images to the console 18, and the reconstruction processor 86 of the console 18 reconstructs the radiographic images in order to generate a plurality of tomographic images.

In the present embodiment, the term "image data" is a general term that covers image data generated by the radiation detector 42, image data sent from the detector controller 64 to the console 18 through the transceivers 68, 70, and image data used in the reconstructing process that is carried out by the reconstruction processor 86.

In other words, the term "image data" refers to images generated on the basis of radiation 40 that passes through the breast 14 and irradiates the radiation detector 42. Consequently, the term "image data" denotes a concept that includes digital data (analog data) representing electric signals converted from the radiation 40 by the radiation detector 42, digital data obtained by converting analog data with an A/D converter, not shown, and image data obtained by a predetermined signal processing technique performed on the digital data by a signal processor, not shown. Therefore, tomographic images are images generated by the reconstructing process that is carried out by the reconstruction processor 86, on the basis of image data generated by the radiation detector 42.

In the present embodiment, the term "radiographic images" refers to image data obtained by the signal processing technique described above. The above description of the arrangement of the breast thickness measuring device 10 signifies a case in which the radiation detector 42 performs a predetermined signal processing technique for generating radiographic images. In particular, the radiation detector 42 includes an A/D converter and a signal processor. The aforementioned signal processing technique is a signal processing technique, which is necessary to obtain images of the breast 14 that can be interpreted and diagnosed by the doctor.

However, the breast thickness measuring device 10 according to the present embodiment is not limited to the arrangement described above. The radiation detector 42 may include at least a function to detect radiation 40 and convert the detected radiation into analog data. Therefore, the A/D converter and the signal processor may be included in a component or components apart from the radiation detector 42.

More specifically, the detector controller 64 may include the signal processor, or may include the A/D converter and the signal processor. In this case, the radiation detector 42 outputs analog data or digital data to the detector controller 64, and the detector controller 64 generates radiographic images. The detector controller 64 transmits the radiographic images to the console 18, and the radiographic images are stored in the projected image memory 76. The detector controller 64 may transmit the digital data in addition to the radiographic images to the console 18, and the digital data and the radiographic images may both be stored in the projected image memory 76.

Alternatively, the A/D converter may be included in the radiation detector 42 or the detector controller 64, and the signal processor may be included in the controller 72 or the reconstruction processor 86 of the console 18. In this case, the detector controller 64 transmits digital data to the console 18, and the digital data are stored in the projected image memory 76. Further, the controller 72 or the reconstruction processor 86 performs a predetermined signal processing technique on the digital data that are stored in the projected image memory 76 in order to generate radiographic images, and the generated radiographic images are stored in the projected image memory 76.

Hereinbelow, unless otherwise noted, a description will be given in which the radiation detector 42 generates the radiographic images.

[Operations of Breast Thickness Measuring Device (Breast Thickness Measuring Method)]

The breast thickness measuring device 10 according to the present embodiment is arranged as described above. Operations of the breast thickness measuring device 10 (breast thickness measuring method) will be described below with reference to FIGS. 5 through 7. As necessary, in describing such operations, FIGS. 1 through 4 may also be referred to. A tomosynthesis image capturing process, in which the radiation source 28 is moved within a range between position B and position C and radiation 40 is applied from different angles θ to the breast 14 in the compressed state, will be described below.

Figure 5:
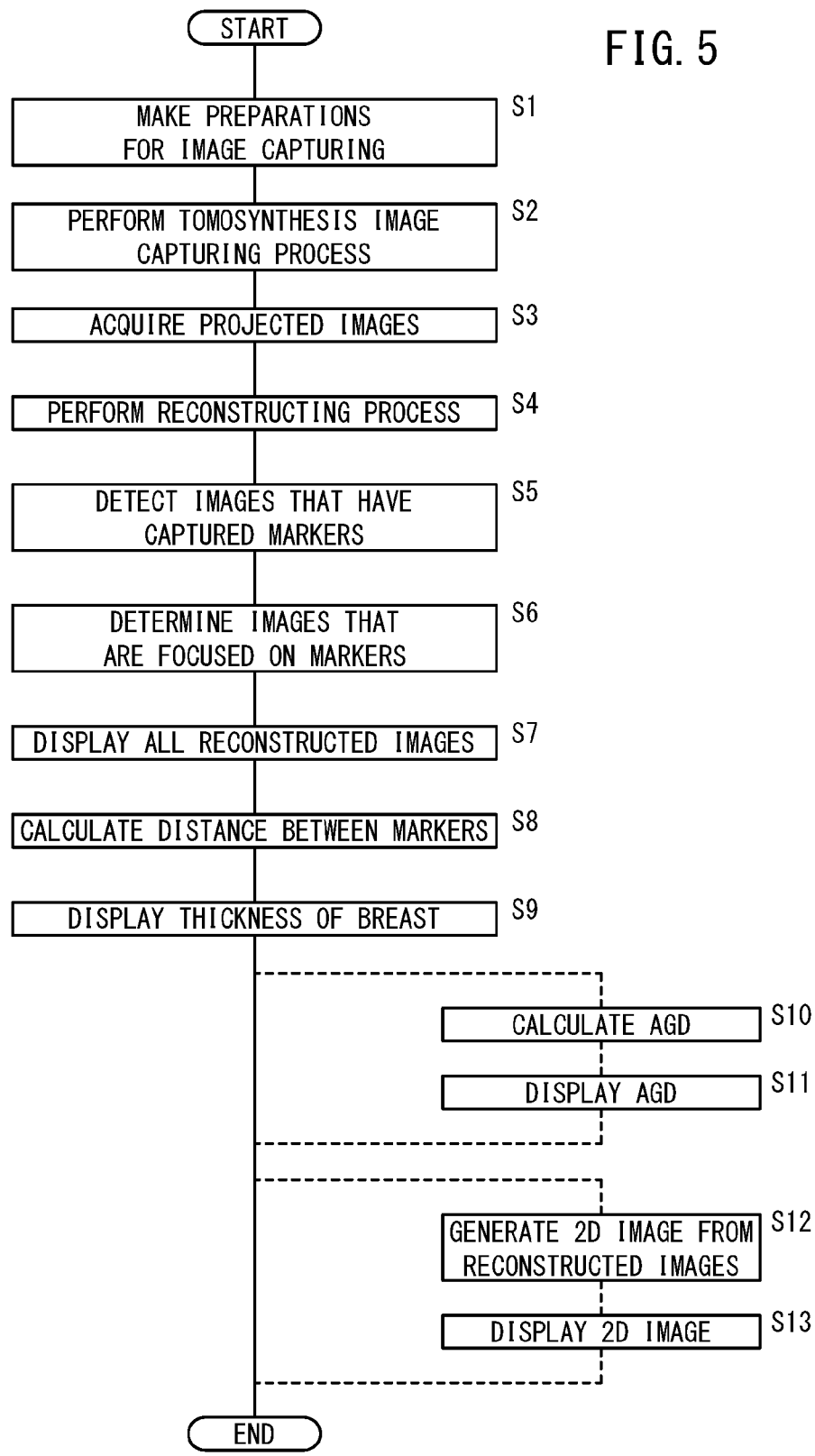
FIG. 5 is a flowchart of an operation sequence of the breast thickness measuring device shown in FIG. 4.

In step S1, as shown in FIG. 5, the radiological technician operates the input operation panel 82 (see FIG. 4) of the console 18 in order to set ID information of the subject 12, in addition to an image capturing method and image capturing conditions for the breast 14. The ID information is information that identifies the subject 12, such as the name, age, etc., of the subject 12.

The controller 72 controls the display unit 84 to display the ID information, the image capturing method, and the image capturing conditions that have been set, and temporarily stores the image capturing conditions in the image capturing condition memory 74. The radiological technician confirms the information that is displayed on the display unit 84 and, as necessary, may add to or change such information using the input operation panel 82. The determined image capturing conditions are transmitted from the transceiver 70 to the transceiver 68 of the radiographic image capturing apparatus 16, and the image capturing conditions are set in the radiation source controller 62.

After the image capturing conditions have been set, the radiographic image capturing apparatus 16 initiates a tomosynthesis image capturing process. At this time, the console 18 sends various items of information to the display control panel 66 of the radiographic image capturing apparatus 16, thus enabling the radiological technician to make adjustments to the radiographic image capturing apparatus 16 while confirming the displayed information.

First, the radiological technician positions the breast 14 of the subject 12 with respect to the radiographic image capturing apparatus 16. More specifically, the radiological technician places the breast 14 on the placement surface 38 of the image capturing table 36, such that the chest wall 48 of the subject 12 is held in contact with the side surface 50 of the image capturing table 36, and the breast 14 to be imaged is disposed bilaterally and symmetrically with respect to the central line 60. Then, the compression plate moving mechanism 46 moves the compression plate 44 gradually toward the image capturing table 36, thereby positioning and holding the breast 14 in a predetermined position between the image capturing table 36 and the compression plate 44.

Next, in accordance with the position of the breast 14, which is compressed and fixed between the image capturing table 36 and the compression plate 44, the rotational shaft 24 is rotated to turn the arm 26, thereby moving the radiation source housing 30 to a predetermined position (image capturing start position) between position B and position C.

In step S2, while the rotational shaft 24 is rotated to turn the arm 26, the radiation source controller 62 controls the radiation source 28 to apply radiation 40 from different angles θ to the compressed breast 14 according to the image capturing conditions.

The first marker 56 and the second marker 58 are disposed within the irradiation range of the radiation 40. Therefore, among the radiation 40 that is emitted from the radiation source 28 and applied to the compression plate 44, a portion of the radiation 40, which is applied to the first marker 56, is absorbed by the first marker 56, and the remainder of such radiation 40 is applied to the breast 14.

Among the radiation 40 that is transmitted through the breast 14 and reaches the placement surface 38 of the image capturing table 36, a portion of the radiation 40, which is applied to the second marker 58, is absorbed by the second marker 58, and the remainder of such radiation 40 reaches the radiation detector 42. Therefore, the radiation detector 42 detects the radiation 40 that has reached the radiation detector 42, and converts the detected radiation 40 into a radiographic image. The detector controller 64 acquires the radiographic image from the radiation detector 42.

As described above, the radiation source 28 applies radiation 40 from different angles θ to the breast 14 while moving between position B and position C. Consequently, each time that the radiation source 28 applies radiation 40 to the breast 14, the detector controller 64 acquires a radiographic image, which is converted from the radiation 40 by the radiation detector 42. Therefore, upon completion of the tomosynthesis image capturing process in step S2, the detector controller 64 acquires a plurality of radiographic images of the breast 14.

In step S3, the detector controller 64 transmits the acquired radiographic images to the console 18 through the transceivers 68, 70. In a case where the controller 72 receives the radiographic images, the received radiographic images are stored in the projected image memory 76. At this time, the projected image memory 76 also stores various items of information assigned to the radiographic images, such as numbers, file names, headers, or the like.

In step S4, the reconstruction processor 86 reads the radiographic images that are stored in the projected image memory 76, reconstructs the read radiographic images in order to generate a plurality of tomographic images, and stores the generated tomographic images in the tomographic image memory 78. At this time, the tomographic image memory 78 also stores various items of information assigned to the tomographic images, such as numbers, file names, headers, or the like.

Figure 6:
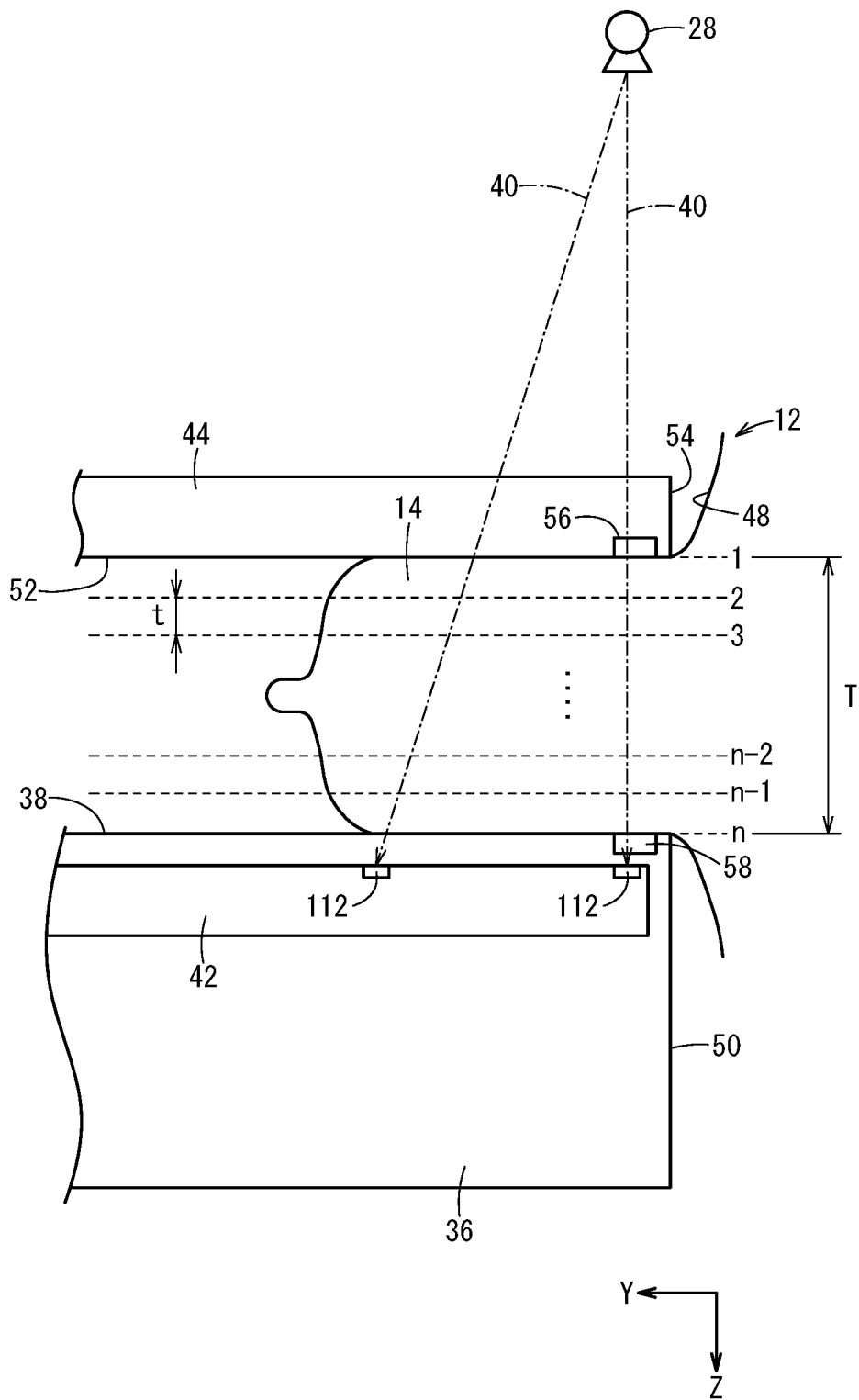
FIG. 6 is a view schematically illustrating slice intervals of tomographic images.
Figure 7:
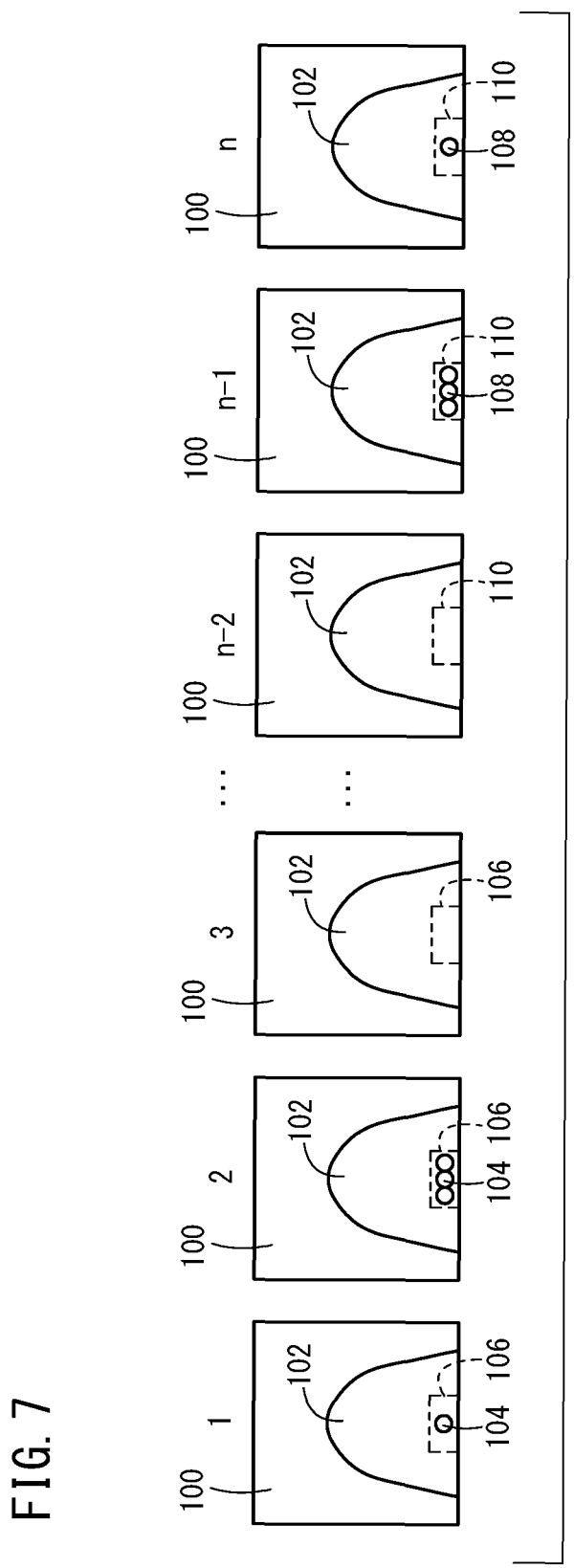
FIG. 7 is a view illustrating the tomographic images.

FIG. 6 is a view in which slice intervals of tomographic images, which are generated at the time that the reconstruction processor 86 (see FIG. 4) performs the reconstructing process, are illustrated. FIG. 7 is a view illustrating the tomographic images generated by the reconstructing process.

The reconstruction processor 86 generates a plurality of tomographic images at given slice intervals t along the direction of the arrow Z. Each of the tomographic images is an image sliced parallel to the placement surface 38 of the image capturing table 36. The slice intervals t are pre-adjusted using a commercially available calibration phantom (geometric calibration phantom), not shown, and are stored in the image capturing condition memory 74, for example.

In FIG. 6, on the assumption that the number of tomographic images sliced between the compression surface 52 of the compression plate 44 and the placement surface 38 of the image capturing table 36 is n, and the tomographic images are given numbers 1, 2, 3, . . . , (n−2), (n−1), and n, respectively, from the compression surface 52 to the placement surface 38, then the first through nth tomographic images are as shown in FIG. 7.

In FIG. 7, each of the tomographic images is denoted by 100 and includes a breast image 102 representing the breast 14. The first and second tomographic images 100 include a marker image 104 representing the first marker 56. The areas shown by the broken lines in the first and second tomographic images 100 are referred to as marker image display areas 106 in which the marker image 104 can be included.

The first tomographic image 100 includes a clearly visible circle representing the first marker 56 as the marker image 104 in the marker image display area 106. The second tomographic image 100 includes a plurality of blurred circles representing the first marker 56 as the marker image 104 in the marker image display area 106. Therefore, the first tomographic image 100 can be interpreted as a tomographic image that is focused on the first marker 56, whereas the second tomographic image 100 can be interpreted as a tomographic image that is not focused on the first marker 56.

The (n−1)th and nth tomographic images 100 include a marker image 108 representing the second marker 58. The areas shown by the broken lines in the (n−1)th and nth tomographic images 100 are referred to as marker image display areas 110 in which the marker image 108 can be included.

The nth tomographic image 100 includes a clearly visible circle representing the second marker 58 as the marker image 108 in the marker image display area 110. The (n−1)th tomographic image 100 includes a plurality of blurred circles representing the second marker 58 as the marker image 108 in the marker image display area 110. Therefore, the nth tomographic image 100 can be interpreted as a tomographic image that is focused on the second marker 58, whereas the (n−1)th tomographic image 100 can be interpreted as a tomographic image that is not focused on the second marker 58.

The third through (n−2)th tomographic images 100 include the breast image 102 only, with no marker images 104, 108 included in the marker image display areas 106, 110. Therefore, the third through (n−2)th tomographic images 100 can be interpreted as tomographic images that are sliced at vertical positions, which differ from the positions of the first marker 56 and the second marker 58.

In FIG. 6, the size of the first marker 56 and the size of the second marker 58 along the horizontal direction (the direction of the arrow X and the direction of the arrow Y) is illustrated as a size that depends on a single pixel 112, which is part of the radiation detector 42 for converting radiation 40 into electric signals. According to the present embodiment, the size of the first marker 56 and the size of the second marker 58 may be of a size such that tomographic images 100 are produced that are focused on the first marker 56 and the second marker 58, e.g., may be a diameter ranging from 100 μm to several mm. Therefore, the size of the first marker 56 and the size of the second marker 58 may be of a size as large as a single pixel or a size as large as several pixels.

According to the present embodiment, at least two tomographic images 100 may be acquired, including respective marker images 104, 108 that are focused on the first marker 56 and the second marker 58. Consequently, instead of the tomographic images 100 shown in FIG. 7, the reconstruction processor 86 may generate the first tomographic image 100 and the nth tomographic image 100, which include the focused marker images 104, 108, as well as the second through (n−1)th tomographic images 100, which do not include the marker images 104, 108.

In step S5, the marker detector 88 detects the tomographic images 100, which include the marker images 104 and 108, from among the tomographic images 100 that are stored in the tomographic image memory 78. For example, in a case where the tomographic images 100 shown in FIG. 7 are stored in the tomographic image memory 78, the marker detector 88 detects the first and second tomographic images 100, which include the marker image 104, and the (n−1)th and nth tomographic images 100, which include the marker image 108.

In step S5, rather than performing the process described above, the marker detector 88 may detect the first and second tomographic images 100, which include the marker image 104, and the (n−1)th and nth tomographic images 100, which include the marker image 108, by specifying various items of information that are assigned to the first and second tomographic images 100, which include the marker image 104 (the numbers "1" and "2" are indicative of the tomographic images 100, the file names, or headers or the like of the tomographic images 100), and various items of information that are assigned to the (n−1)th and nth tomographic images 100, which include the marker image 108 (the numbers "n−1" and "n" are indicative of the tomographic images 100, the file names, or headers or the like of the tomographic images 100).

In step S6, from among the tomographic images 100 detected by the marker detector 88, the marker determiner 90 selects the tomographic image 100 that is focused on the first marker 56 and the tomographic image 100 that is focused on the second marker 58. More specifically, the marker determiner 90 selects the first tomographic image 100 from among the first and second tomographic images 100, and further selects the nth tomographic image 100 from among the (n−1)th and the nth tomographic images 100.

In step S6, rather than performing the process described above, the marker determiner 90 may select the tomographic image 100, which is focused on the first marker 56, and the tomographic image 100, which is focused on the second marker 58, by specifying various items of information assigned to the tomographic image 100 that is focused on the first marker 56 and the tomographic image 100 that is focused on the second marker 58.

In step S7, the display unit 84 displays all of the tomographic images 100 that are stored in the tomographic image memory 78.

In step S8, the compressed thickness calculator 92 calculates the compressed thickness T of the breast 14 using the tomographic image 100 (first tomographic image 100) that is focused on the first marker 56 and the tomographic image 100 (nth tomographic image 100) that is focused on the second marker 58, which have been selected by the marker determiner 90 in step S6.

The first tomographic image 100, which is focused on the first marker 56, can be regarded as a tomographic image sliced at the vertical position of the first marker 56. The nth tomographic image 100, which is focused on the second marker 58, can be regarded as a tomographic image sliced at the vertical position of the second marker 58. The first marker 56 is a marker that is embedded in the compression plate 44, so as to lie substantially flush with the compression surface 52. The second marker 58 is a marker that is embedded in the image capturing table 36, so as to lie substantially flush with the placement surface 38. Therefore, the compressed thickness calculator 92 calculates the compressed thickness T according to the following equation (1).

$$T = t \times (n-1) \quad (1)$$

In step S8, rather than performing the process described above, the compressed thickness calculator 92 may calculate the compressed thickness T by using various items of information assigned to the tomographic image 100 that is focused on the first marker 56 and the tomographic image 100 that is focused on the second marker 58. More specifically, in a case where the number given to the tomographic image 100 that is focused on the first marker 56 is n1, and the number given to the tomographic image 100 that is focused on the second marker 58 is n2, the compressed thickness calculator 92 may calculate the compressed thickness T according to the following equation (2).

$$T = t \times (n2 - n1) \quad (2)$$

In the example shown in FIGS. 6 and 7, since n1=1 (first tomographic image 100) and n2=n (nth tomographic image), the compressed thickness calculator 92 can easily calculate the compressed thickness T according to equation (2). In equation (2), (n2−n1) represents the number of tomographic images 100 from the n1th tomographic image 100 to the n2th tomographic image 100.

Assuming that the numbers 1, 2, 3, ..., 100 are assigned to a plurality of tomographic images 100, the tomographic image 100 in which the first marker 56 is clearest is the 5th tomographic image, and the tomographic image 100 in which the second marker 58 is clearest is the 95th tomographic image, the compressed thickness calculator 92 is capable of determining the compressed thickness T according to equation (2), where n1=5 and n2=95, i.e., T=t×(95−5).

In step S9, the display unit 84 displays the compressed thickness T that was calculated by the compressed thickness calculator 92. Thus, the radiological technician is capable of accurately grasping the thickness (compressed thickness) T of the breast 14 in the compressed state.

According to the present embodiment, steps S10 through S13 may be carried out after step S9, as necessary.

In step S10, the AGD calculator 94 calculates the AGD of the breast 14 on the basis of the compressed thickness T that was calculated by the compressed thickness calculator 92. In step S11, the display unit 84 displays the AGD that was calculated by the AGD calculator 94. Thus, the radiological technician is capable of grasping the accurate AGD of the breast 14 in the compressed state.

In step S12, the 2D image generator 96 performs a predetermined addition process on the tomographic images 100 that are stored in the tomographic image memory 78 in order to generate a 2D image, and the generated 2D image is stored in the 2D image memory 80. In step S13, the display unit 84 displays the 2D image stored in the 2D image memory 80. Thus, the radiological technician is capable of observing the 2D image of the breast 14 in the compressed state. In a case where the console 18 transmits the 2D image to the viewer through the in-hospital network, the doctor is able to interpret and diagnose the 2D image that is displayed on the viewer.

Details of the process for generating the 2D image in step S12 will be described later.

Advantages of the Present Embodiment

As described above, the breast thickness measuring device 10 and the breast thickness measuring method according to the present embodiment perform a tomosynthesis image capturing process for applying radiation 40 from a plurality of different angles θ to the breast 14 in the compressed state, and a plurality of tomographic images 100 are generated by reconstructing radiographic images obtained by the tomosynthesis image capturing process.

The first marker 56 is provided on the compression plate 44, whereas the second marker 58 is provided on the image capturing table 36. Therefore, the tomographic image 100 that is focused on the first marker 56 is a tomographic image of an upper end of the breast 14 along the thickness-wise direction (the direction of the arrow Z) of the breast 14. The tomographic image 100 that is focused on the second marker 58 is a tomographic image of a lower end of the breast 14 along the direction of the arrow Z.

Consequently, using the tomographic image 100 that is focused on the first marker 56 and the tomographic image 100 that is focused on the second marker 58, it is possible to directly calculate the thickness (compressed thickness) T of the breast 14 in the compressed state.

In addition, the first marker 56 and the second marker 58 are disposed on the side of the chest wall 48 of the subject 12. Therefore, the present embodiment allows the compressed thickness T to be calculated more accurately than with the technologies disclosed in the publications referred to above.

Therefore, according to the present embodiment, it is possible to accurately grasp the compressed thickness T of the breast.

More specifically, from among the tomographic images 100, the marker determiner 90 selects the tomographic image 100 that is focused on (the marker image 104 representing) the first marker 56, and also, from among the tomographic images 100, selects the tomographic image 100 that is focused on (the marker image 108 representing) the second marker 58. The compressed thickness calculator 92 then calculates the compressed thickness T based on the two tomographic images 100 that have been selected by the marker determiner 90. The tomographic images can be regarded as tomographic images sliced at vertical positions of the first marker 56 and the second marker 58. The compressed thickness T can be calculated highly accurately by selecting the two tomographic images 100 that are focused on the first marker 56 and the second marker 58.

The tomographic images 100 represent images at discrete cross sections, which are spaced at predetermined slice intervals t. Consequently, depending on the slice intervals t or the slicing method, it is conceivable that a tomographic image 100 may not necessarily be obtained at the vertical position of the first marker 56 or the second marker 58. According to the present embodiment, therefore, the marker determiner 90 selects, from among the tomographic images 100 that have captured (the marker image 104 representing) the first marker 56, a tomographic image 100 in which the first marker 56 is clearly visible as the tomographic image 100 that is focused on the first marker 56. Similarly, the marker determiner 90 also selects, from among the tomographic images 100 that have captured (the marker image 108 representing) the second marker 58, a tomographic image 100 in which the second marker 58 is clearly visible as the tomographic image 100 that is focused on the second marker 58.

By selecting the tomographic image 100 of the first marker 56 and the tomographic image 100 of the second marker 58 in this manner, the accuracy with which the compressed thickness T is calculated is prevented from becoming lowered on account of the slice intervals t and the slicing method. Assuming that the tomographic image 100 at the vertical position of the first marker 56 and the tomographic image 100 at the vertical position of the second marker 58 are obtained, then naturally, by using such tomographic images 100, it is possible to calculate the compressed thickness T with high accuracy.

Various items of information with respect to the tomographic images 100, such as numbers, file names, headers, or the like of the tomographic images 100, are assigned to the tomographic images 100, and such items are stored in the tomographic image memory 78. According to the present embodiment, therefore, the process of detecting tomographic images 100 by the marker detector 88, the process of selecting tomographic images 100 by the marker determiner 90, and the process of calculating the compressed thickness T by the compressed thickness calculator 92 may be carried out using the various items of information that are assigned to the tomographic images 100.

More specifically, in a case where the tomographic images 100 and the various items information are stored in the tomographic image memory 78, the marker detector 88 may detect the tomographic images 100, which have captured the first marker 56, and the tomographic images 100, which have captured the second marker 58, by specifying the various items of information assigned to the tomographic images 100 that have captured the first marker 56 and the tomographic images 100 that have captured the second marker 58.

From among the tomographic images 100 that have captured the first marker 56 and the tomographic images 100 that have captured the second marker 58, the marker determiner 90 may select the tomographic image 100 that is focused on the first marker 56 and the tomographic image 100 that is focused on the second marker 58, by specifying various items of information that are assigned to the tomographic image 100 that is focused on the first marker 56 and the tomographic image 100 that is focused on the second marker 58.

Furthermore, the compressed thickness calculator 92 may calculate the compressed thickness T using the information that is assigned to the tomographic image 100 that is focused on the first marker 56 and the tomographic image 100 that is focused on the second marker 58.

Consequently, the process of detecting the tomographic images 100 by the marker detector 88, the process of selecting the tomographic images 100 by the marker determiner 90, and the process of calculating the compressed thickness T by the compressed thickness calculator 92 include processes involving various items of information assigned to the tomographic images 100. For example, the phrase "calculating the compressed thickness T based on the tomographic image 100 that is focused on the first marker 56 and the tomographic image 100 that is focused on the second marker 58" implies a concept that includes calculation of the compressed thickness T using the various items of information assigned to the tomographic images 100.

In as much as the compressed thickness calculator 92 calculates the compressed thickness T according to equation (1) or (2), the compressed thickness calculator 92 can reliably calculate the actual thickness of the breast 14 in the compressed state.

The reconstruction processor 86 reconstructs the radiographic images in order to generate tomographic images 100, such that the tomographic images 100 become tomographic images sliced parallel to the image capturing table 36. Therefore, the marker detector 88 is capable of easily detecting tomographic images 100, which include the first marker 56 or the second marker 58.

Since the first marker 56 and the second marker 58 are disposed in superposed relation as viewed as a planar view, the burden imposed by the correcting process for generating a 2D image from the tomographic images 100 is reduced.

The burden imposed by the aforementioned correcting process is further lessened due to the fact that the image capturing table 36, the radiation detector 42, the compression plate 44, the first marker 56, and the second marker 58 are disposed on the vertical axis 32 at the central angle (θ=0°) of the radiation source 28.

Further, since the AGD calculator 94 calculates the AGD based on the compressed thickness T, which is calculated by the compressed thickness calculator 92, it is possible to grasp an accurate radiation dose to which the breast 14 is exposed. Consequently, provided that the compressed thickness T is calculated accurately from the tomographic images 100 obtained by the tomosynthesis image capturing process, and the AGD is calculated accurately on the basis of the calculated compressed thickness T, in a case where a normal image capturing process is carried out on the breast 14 after the tomosynthesis image capturing process, on the basis of the AGD, it is possible to accurately calculate the required dose of the radiation 40 to be applied in the normal image capturing process.

Modifications of the Present Embodiment

Modifications (first through sixth modifications) of the breast thickness measuring device 10 and the breast thickness measuring method according to the present embodiment will be described below with reference to FIGS. 8 through 19.

First Modification

Figure 8:
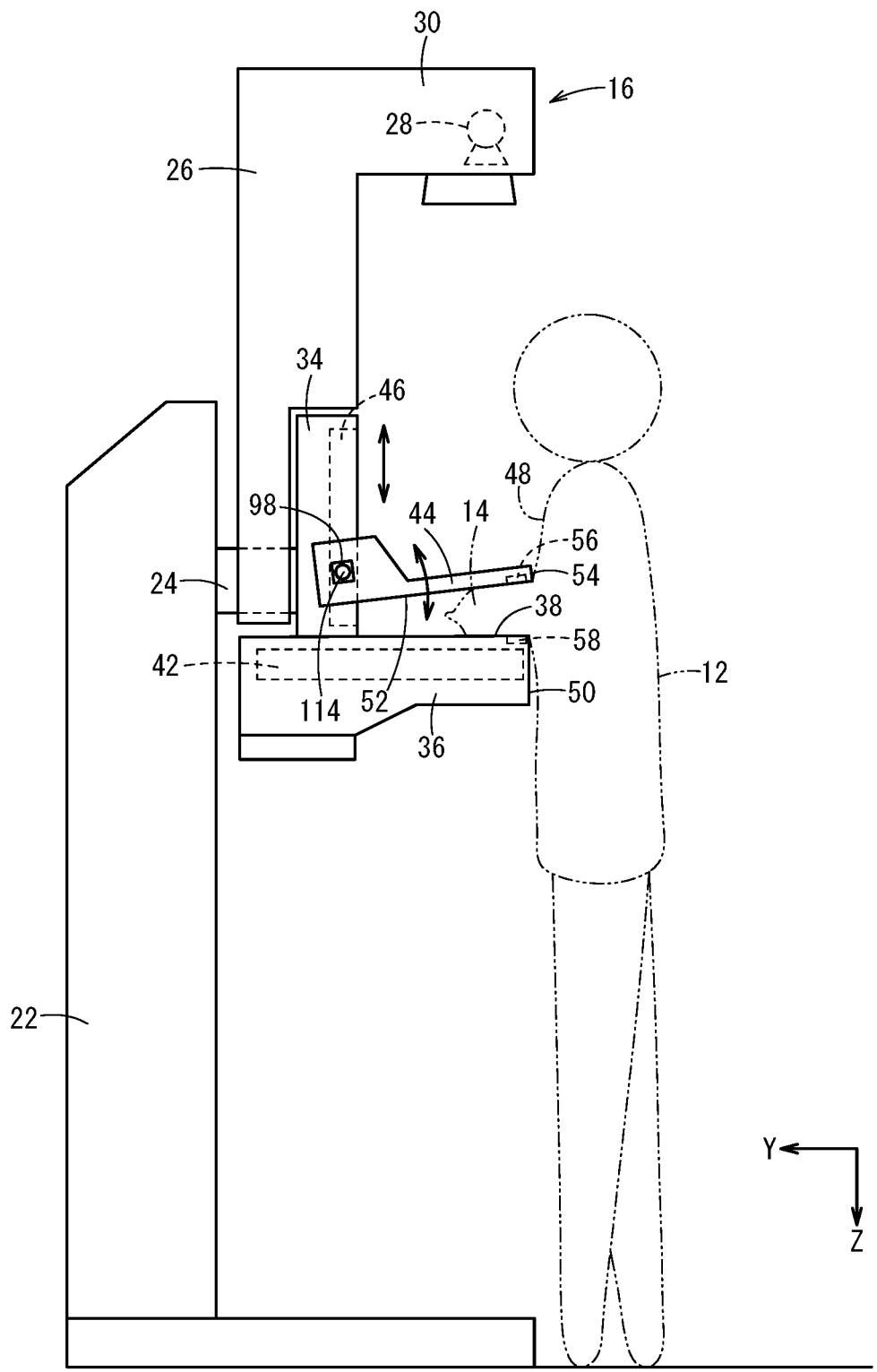
FIG. 8 is a side elevational view illustrating another arrangement (first modification) of the radiographic image capturing apparatus shown in FIGS. 1 and 2.
Figure 9:
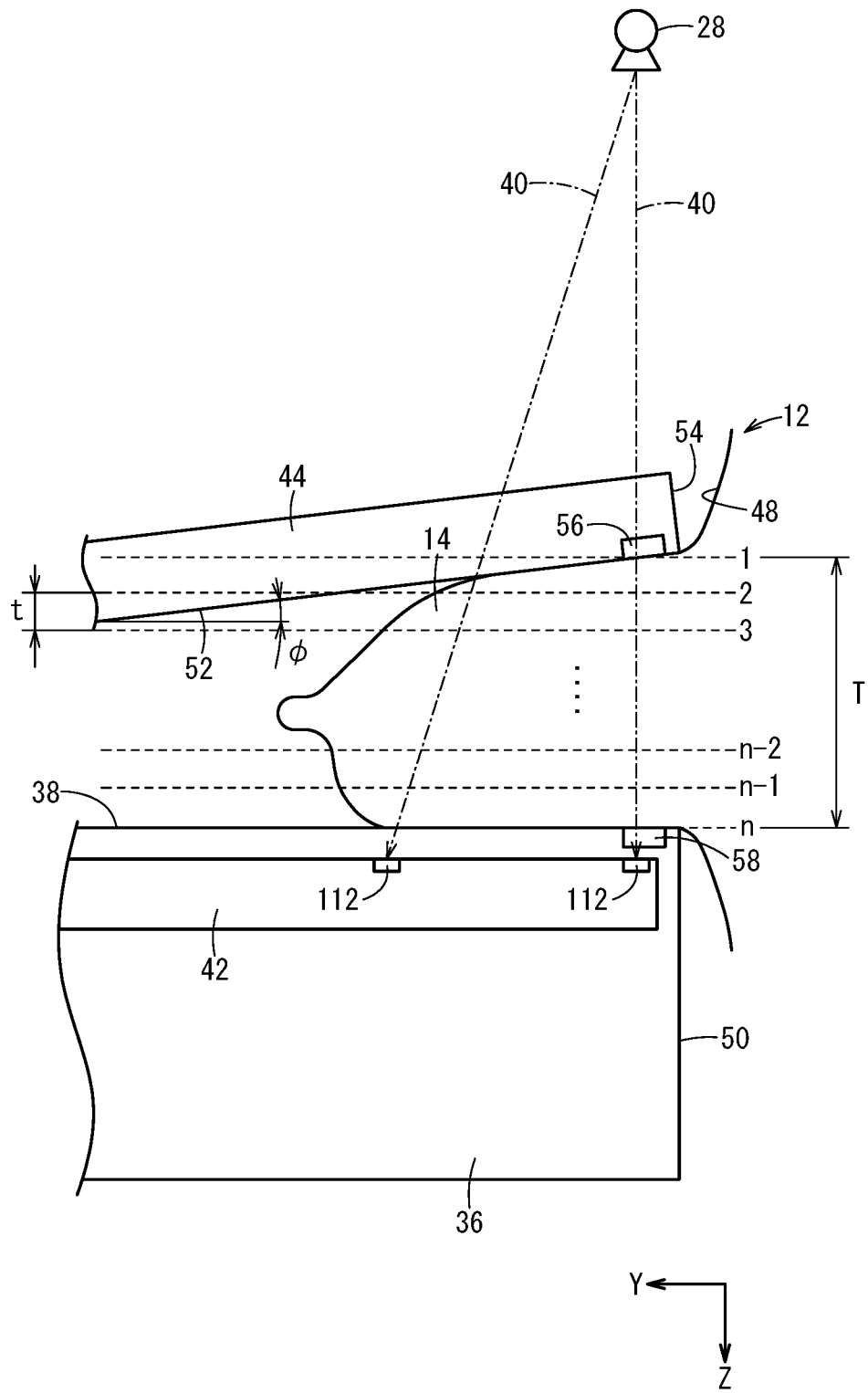
FIG. 9 is a view schematically illustrating slice intervals of tomographic images.
Figure 10:
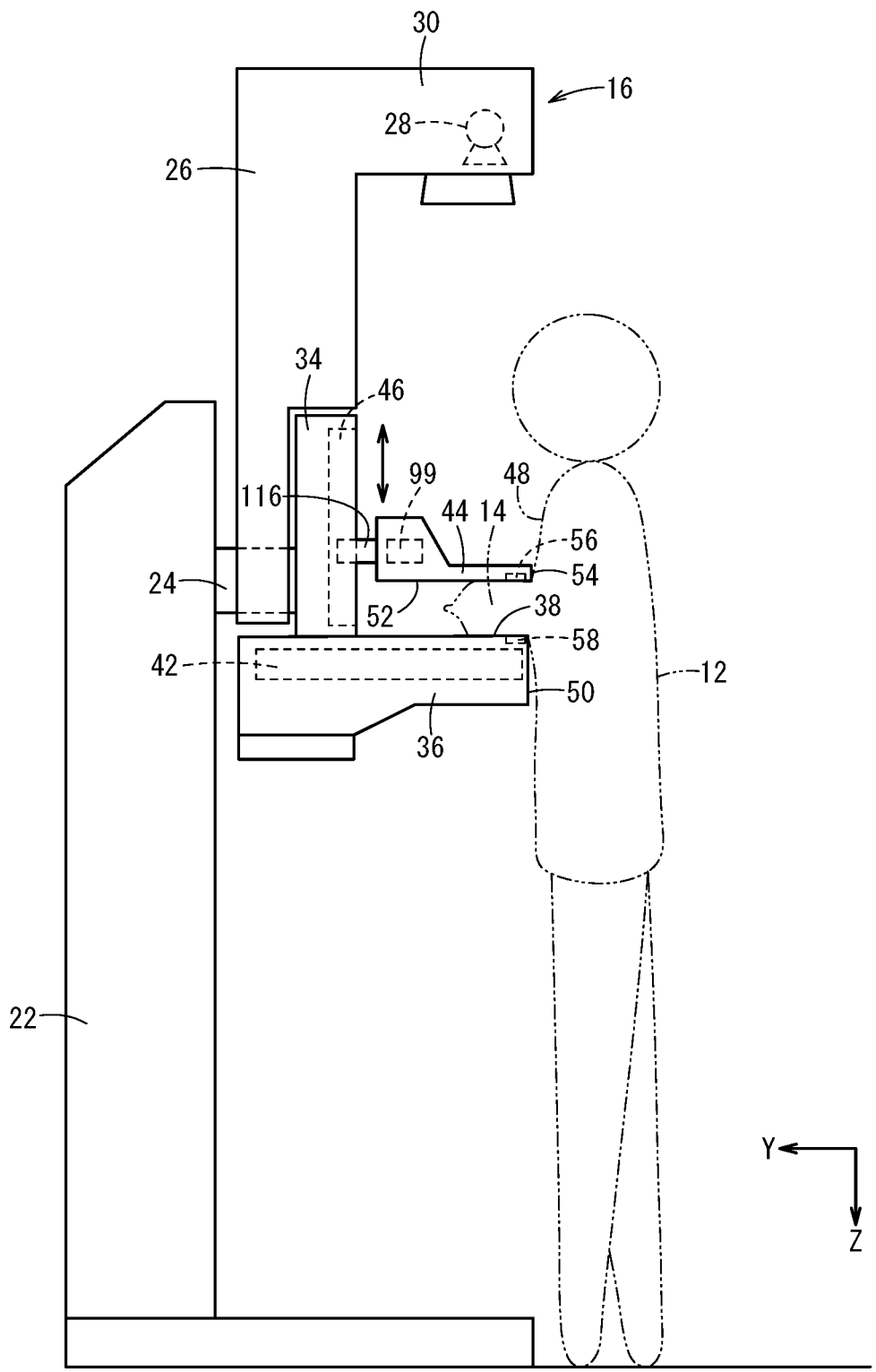
FIG. 10 is a side elevational view illustrating still another arrangement (second modification) of the radiographic image capturing apparatus shown in FIGS. 1 and 2.

According to the first modification, as shown in FIGS. 8 and 9, a shaft 114 is provided on a proximal end portion of the compression plate 44, and the compression plate 44 is arranged so as to be capable of moving angularly about the shaft 114. Therefore, in a case where the compression plate 44 is lowered toward the image capturing table 36 by the compression plate moving mechanism 46, and is brought into contact with the breast 14, the side of the compression plate 44 proximate the side surface 54 turns counterclockwise as shown in FIGS. 8 and 9 (toward the radiation source 28) about the shaft 114. Thus, the compression plate 44 compresses the breast 14 while being tilted along the breast 14. The angle sensor 98 is mounted on the shaft 114 for detecting the angle φ of tilt of the compression plate 44 with respect to the horizontal plane (i.e., the angle of the compression plate 44 before the compression plate 44 contacts the breast 14).

According to the first modification, the first marker 56 also is provided on the compression plate 44 proximate the side surface 54 thereof, and the second marker 58 also is provided on the image capturing table 36 proximate the side surface 50 thereof. Therefore, the compressed thickness T is represented by the distance between the compression surface 52 of the tilted compression plate 44 at the side surface 54, and the placement surface 38 of the image capturing table 36. In addition, according to the first modification, the reconstruction processor 86 reconstructs the radiographic images in order to generate tomographic images 100 in such a manner that the tomographic images 100 are sliced parallel to the placement surface 38.

In a case where the compression plate 44 compresses the breast 14 in a tilted state, the technologies disclosed in the above publications detect the position of the compression plate 44 at a proximal end portion thereof. Therefore, in the event that the compressed thickness T is estimated from the detected position of the compression plate 44 at the proximal end portion, a large estimation error occurs, making it impossible to acquire an accurate estimation of the compressed thickness T.

According to the first modification, the first marker 56 and the second marker 58 are disposed on the side of the chest wall 48 of the subject 12, and the compressed thickness T is calculated using tomographic images 100 that have captured the first marker 56 and the second marker 58. In other words, according to the first modification, the thickness (compressed thickness) T of the breast 14, which is actually compressed, is directly measured from the tomographic images 100. Therefore, according to the first modification, it is possible to measure the compressed thickness T more accurately than with the technologies disclosed in the above publications.

Second Modification

According to the second modification, as shown in FIGS. 10 through 13, the compression plate 44 is mounted on the holder 34 by a rotational shaft 116, and the compression plate 44 is arranged so as to be angularly movable about the rotational shaft 116. The angle α of tilt of the compression plate 44 with respect to the horizontal direction (the direction of the arrow X and the direction of the arrow Y) is detected by the angle sensor 99.

Figure 12:
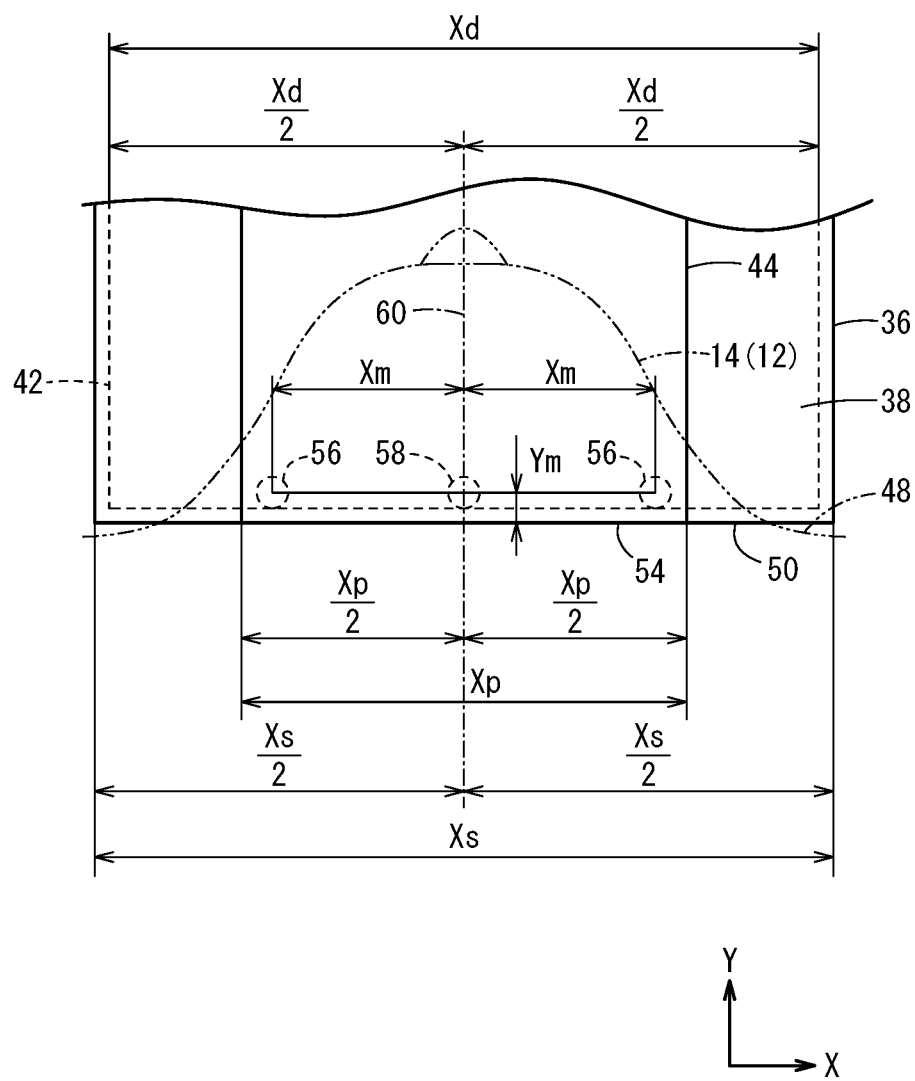
FIG. 12 is a planar view illustrating chest-wall sides of a compression plate and an image capturing table.

According to the second modification, first markers 56 are disposed on respective left and right corners (angular portions) along the direction of the arrow X proximate the side surface 54 of the compression plate 44. More specifically, according to the second modification, as shown in FIG. 12, the two first markers 56 are embedded in the compression plate 44 so as to lie substantially flush with the compression surface 52 at positions spaced Xm to the left and right from the central line 60, and also spaced Ym back from the side surface 54 toward the rotational shaft 24. According to the second modification, therefore, a first marker 56 is not disposed on the central line 60. Furthermore, according to the second modification, the two first markers 56 are positioned over the radiation detector 42 as viewed as a planar view, and are disposed within the irradiation range of the radiation 40.

According to the second modification, the second marker 58 is disposed in the same position as the second marker 58 shown in FIGS. 1 through 3 (i.e., at a position located on the central line 60 and spaced Ym back from the side surface 50 toward the rotational shaft 24). As described above, since the image capturing table 36 is harder than the compression plate 44, the second marker 58 is disposed only in one location on the image capturing table 36.

Figure 11:
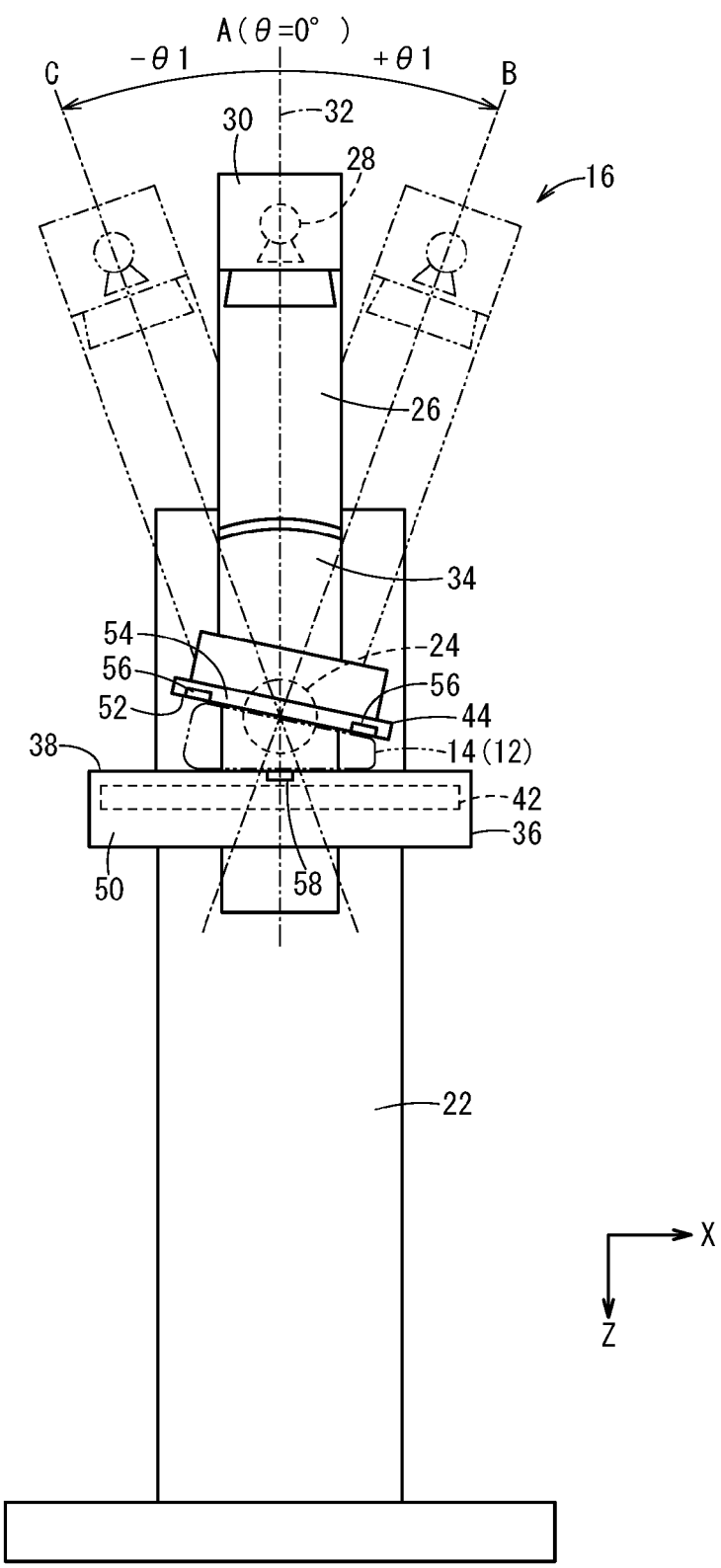
FIG. 11 is a front elevational view of the radiographic image capturing apparatus shown in FIG. 10.
Figure 13:
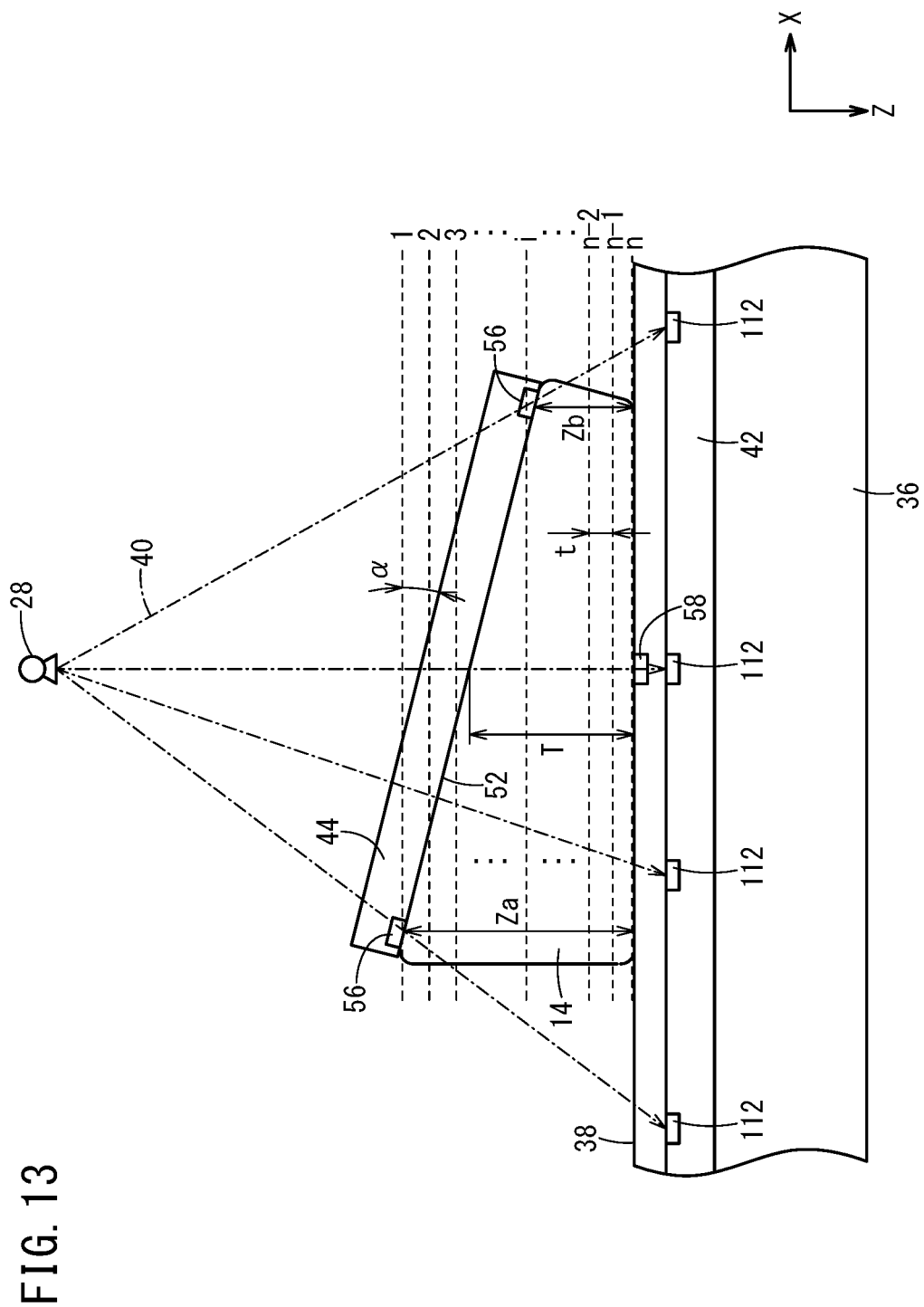
FIG. 13 is a view schematically illustrating slice intervals of tomographic images.

As shown in FIGS. 11 and 13, according to the second modification, while the rotational shaft 116 is rotated to turn the compression plate 44 (i.e., to tilt the compression plate 44 laterally along the direction of the arrow X), the compression plate 44 is lowered toward the image capturing table 36, thereby compressing and holding the breast 14 in a laterally tilted state.

According to the second modification, assuming that the distance between the central position of the compression surface 52 of the compression plate 44 on the vertical axis 32, and the central position of the placement surface 38 of the image capturing table 36 is regarded as the compressed thickness T (average value) of the breast 14, then the compressed thickness T is expressed by the following equation (3)

$$T=(Za+Zb)/2 \quad (3)$$

where Za represents the distance between the left first marker 56 shown in FIGS. 11 and 13 and the placement surface 38, and Zb represents the distance between the first marker 56 shown on the right in FIGS. 11 and 13 and the placement surface 38.

More specifically, the two first markers 56 are disposed on the compression plate 44 and spaced equal distances (Xm) from the central line 60 to the left and right. Therefore, the compressed thickness T at an intermediate position between the two first markers 56 can easily be calculated from the two distances Za, Zb.

The distance Za can be calculated according to the following equation (4) using the above equation (1), or according to the following equation (5) using the above equation (2), on the basis of the first tomographic image 100 that has captured the left first marker 56 and the nth tomographic image 100 that has captured the second marker 58.

$$Za=t\times(n-1) \quad (4)$$

$$Za=t\times(n2-n1) \quad (5)$$

The distance Zb can be calculated according to the following equation (6) using the above equation (1) or (2), as partially modified, on the basis of the ith tomographic image 100 that has captured the right first marker 56 and the nth tomographic image 100 that has captured the second marker 58.

$$Zb=t\times(n-i) \quad (6)$$

Therefore, according to the second modification, the marker detector 88 detects a tomographic image 100 that has captured the left first marker 56 (first tomographic image 100), a tomographic image 100 that has captured the right first marker 56 (ith tomographic image 100), and a tomographic image 100 that has captured the second marker 58 (nth tomographic image 100). From among the tomographic images 100 detected by the marker detector 88, the marker determiner 90 selects the tomographic images 100 that are focused on the left first marker 56, the right first marker 56, and the second marker 58. Then, according to the above equations (3) through (6), the compressed thickness calculator 92 calculates the distances Za, Zb and the compressed thickness T.

According to the second modification, as described above, even though the breast 14 is compressed and held by the compression plate 44, which is tilted laterally along the direction of the arrow X, the compressed thickness T can accurately be measured because the first markers 56 are provided on left and right sides of the compression plate 44.

Furthermore, according to the second modification, since the distances Za, Zb, which are indicative of the compressed thickness, can be measured, the tilt of the compression plate 44 with respect to the placement surface 38 of the image capturing table 36 (the direction of the arrow X as a horizontal direction) can accurately be calculated from the distances Za, Zb.

Third Modification

Figure 14:
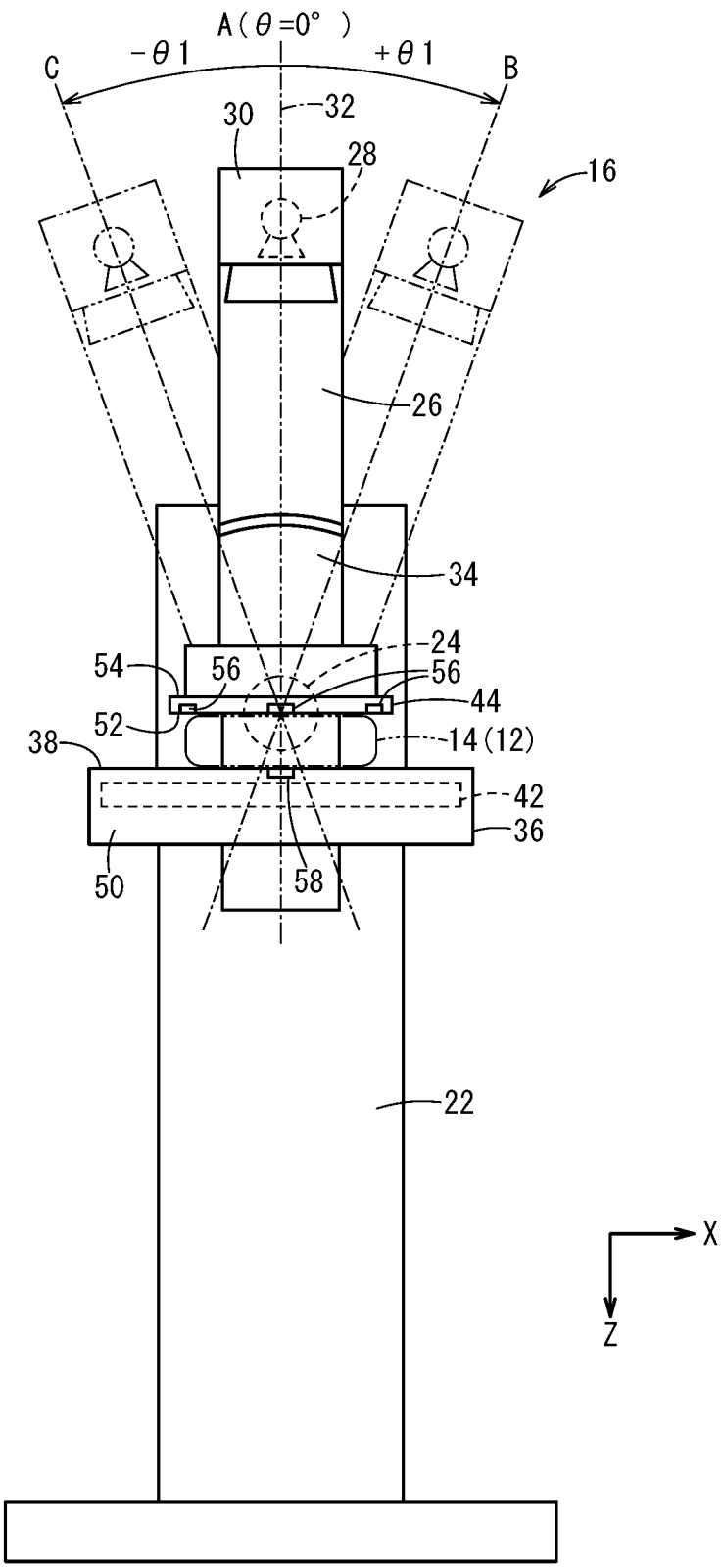
FIG. 14 is a side elevational view illustrating yet another arrangement (third modification) of the radiographic image capturing apparatus shown in FIGS. 1 and 2.
Figure 15:
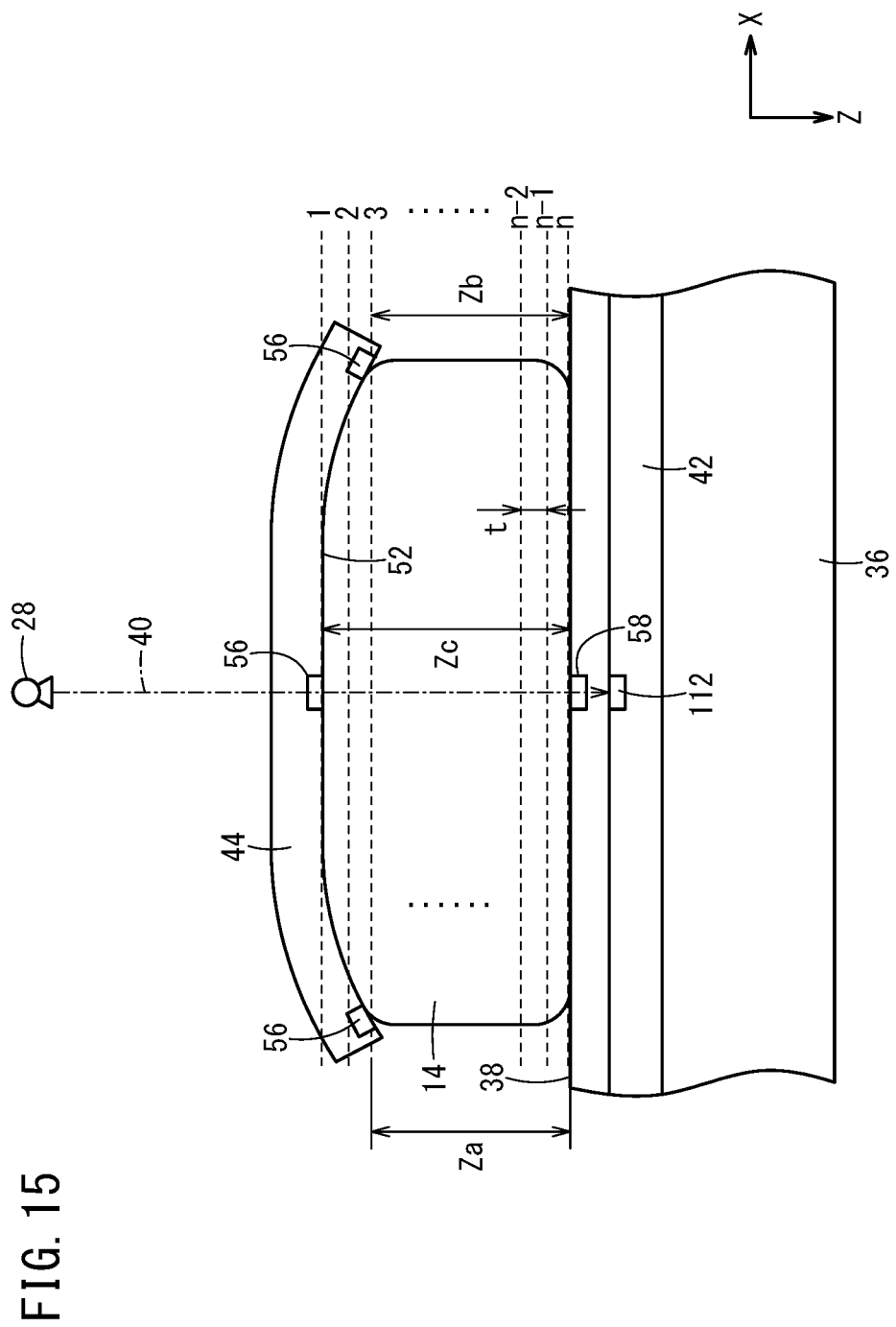
FIG. 15 is a view schematically illustrating slice intervals of tomographic images.

As shown in FIGS. 14 and 15, the third modification differs from the second modification (see FIGS. 10 through 13), in that a further first marker 56 is disposed at a central position (a position on the vertical axis 32) of the compression plate 44 proximate the side surface 54 thereof. Accordingly, the third modification is a combination of the arrangement of the embodiment shown in FIGS. 1 through 3 and the arrangement of the second modification shown in FIGS. 10 through 13.

According to the third modification, as shown in FIG. 15, in the case that the compression plate 44 is curved (curved in an upwardly convex manner as shown in FIG. 15), it is possible to grasp the degree to which the compression plate 44 is distorted.

More specifically, as shown in FIG. 15, assuming that the distance between the central first marker 56 and the placement surface 38 is represented by Zc, the central first marker 56 is captured in the first tomographic image 100, and the left and right first markers 56 are captured in the third tomographic image 100, the distances Za, Zb, Zc are expressed by the following equations (7) and (8).

$$Za=Zb=t\times(n-3) \quad (7)$$

$$Zc=t\times(n-1) \quad (8)$$

In the event that the distances Za, Zb, Zc satisfy the following inequality (9), it can easily be judged that the compression plate 44 is distorted.

$$Zc>(Za+Zb)/2 \quad (9)$$

The marker detector 88 detects the tomographic images 100 that have captured the first markers 56 (first and third tomographic images 100) and the tomographic image 100 that has captured the second marker 58 (nth tomographic image 100). From among the tomographic images 100 detected by the marker detector 88, the marker determiner 90 selects tomographic images 100 that are focused on the first markers 56 and the second marker 58. The compressed thickness calculator 92 detects whether or not the compression plate 44 is distorted according to the above equations (7) through (9).

According to the third modification, as described above, the first markers 56 are provided on left and right corners and on a central area of the compression plate 44 proximate the side surface 54 thereof, while in addition, the second marker 58 is provided on the image capturing table 36 proximate the side surface 50 thereof. Therefore, it is possible to make accurate measurements concerning whether or not the compression plate 44 is distorted. Even though only a single second marker 58 is disposed on the image capturing table 36, because the image capturing table 36 is harder than the compression plate 44, the occurrence of distortions in the compression plate 44 can be measured with high accuracy.

According to the third modification, the compression plate 44 compresses the breast 14 parallel to the placement surface 38 of the image capturing table 36 (i.e., in the direction of the arrow X as a horizontal direction). Even in a case where the compression plate 44 compresses the breast 14 while being tilted with respect to the placement surface 38, as in the case of the second modification (see FIGS. 10 through 13), equation (9) can still be applied.

Fourth Modification

Concerning the fourth modification, details of a process for generating a 2D image by the 2D image generator 96 shown in FIG. 4 (step S12 of FIG. 5) will be described below with reference to FIGS. 16 and 17.

As described above, the 2D image generator 96 performs a predetermined addition process on a plurality of tomographic images 100 to thereby generate a 2D image of the breast 14.

First, problems that are caused in a case where a simple addition process is performed on all of the tomographic images 100 in order to generate the 2D image will be described below.

Figure 16:
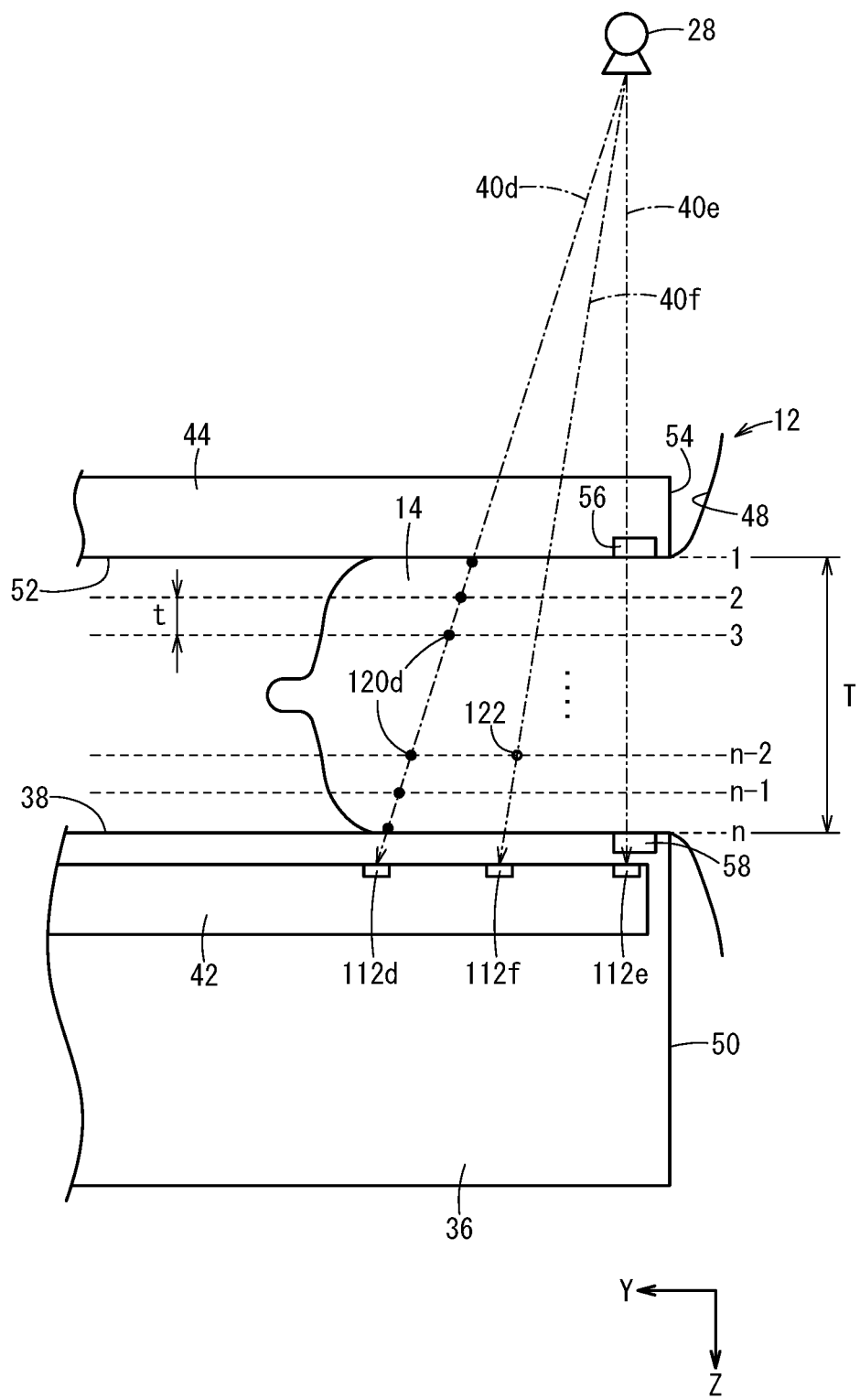
FIG. 16 is a view schematically illustrating a manner in which a 2D image is generated from tomographic images (fourth modification)

As shown schematically in FIG. 16, on the assumption that a pixel depending on a particular location in the 2D image is treated as a pixel 112*d*, then according to the simple addition process for the tomographic images 100, the pixel values at locations 120*d* along a path of radiation 40*d* that is applied to the pixel 112*d* from the radiation source 28 are simply added together, thereby producing a pixel value at a particular location in the 2D image according to the pixel 112*d*.

Therefore, in order to generate the 2D image according to the simple addition process, in the radiation detector 42, the process of simply adding pixel values at the locations 120*d* along the path of the radiation 40*d* is carried out with respect to all of the pixels 112.

However, with the simple addition process, the following problems occur. More specifically, according to the simple addition process, the pixel values at locations 120*d* along the path of the radiation 40*d* are simply added together. Therefore, in a case where radiation 40*e* is applied to the first marker 56 or the second marker 58, the simple addition process is performed along the locations on the path of the radiation 40*e*, at a location in a 2D image corresponding to the pixel 112*e* that is irradiated with the radiation 40*e*. In a case where an abnormal location 122, such as a calcified region, spicula, mass, or the like, is formed in the breast 14, then at a location in a 2D image corresponding to the pixel 112*f* that is irradiated with radiation 40*f* transmitted through the abnormal location 122, the simple addition process is performed on the locations on the path of the radiation 40*f*.

Figure 17:
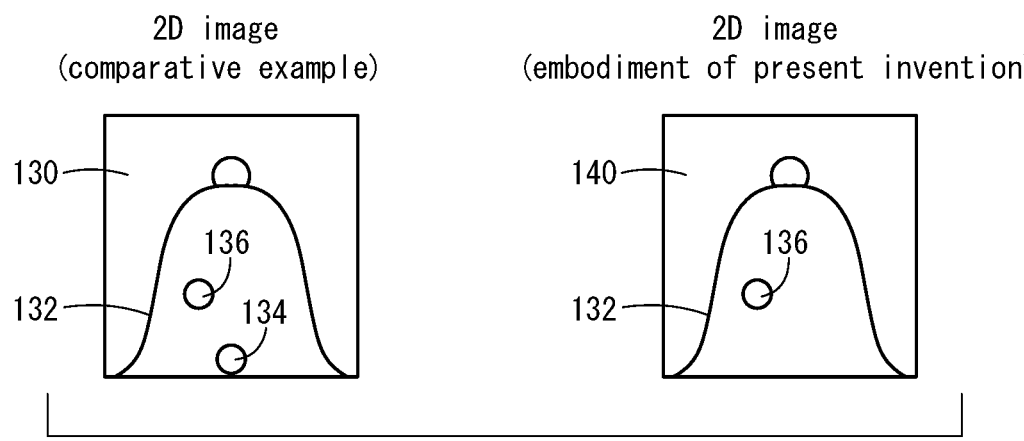
FIG. 17 is a view illustrating 2D images.

Therefore, as shown in FIG. 17, the 2D image 130 (the left image according to a comparative example), which is obtained by the simple addition process, captures both a marker image 134 representing the first marker 56 and the second marker 58, as well as an abnormal image 136 representing the abnormal location 122 in a breast image 132 representing the breast 14. As a result, in a case where the doctor interprets and diagnoses the 2D image 130 that is displayed on the viewer, the doctor may mistake the first marker 56 and the second marker 58 for the abnormal location 122, such as a calcified region, spicula, mass, or the like that is formed in the breast 14. Thus, there is a possibility that the burden on the doctor will increase.

According to the fourth modification, as described in any of paragraphs (1) through (3) below, in step S12 of FIG. 5, the 2D image generator 96 carries out a correcting process for excluding the marker image 134, and generates a 2D image 140 in which only the abnormal image 136 is captured in the breast image 132, as shown on the right in FIG. 17.

(1) From among the tomographic images 100, the 2D image generator 96 simply adds the tomographic images 100 (e.g., the third through (n−2)th tomographic images 100 in FIG. 7) that have not captured (the marker image 104 representing) the first marker 56 or the (marker image 108 representing) the second marker 58, thereby generating the 2D image 140.

(2) From among the tomographic images 100, the 2D image generator 96 performs a first addition process for simply adding the tomographic images 100 for image areas in which the marker images 104, 108 do not exist (areas other than the marker image display areas 106). Then, from among the tomographic images 100, the 2D image generator 96 performs a second addition process for simply adding the marker image display areas 106, 110 of the tomographic images 100 (e.g., the third through (n−2)th tomographic images 100 in FIG. 7) from which the tomographic images 100 that have captured the marker images 104, 108 are excluded. Finally, the 2D image generator 96 combines the two new images, which were obtained by the first addition process and the second addition process, thereby generating the 2D image 140.

(3) From among the tomographic images 100, the 2D image generator 96 performs a correcting process for removing the marker images 104, 108 on the tomographic images 100 that have captured the marker images 104, 108. Then, the 2D image generator 96 simply adds the tomographic images 100 that have not captured the marker images 104, 108, and the tomographic images 100 on which the correcting process has been performed, thereby generating the 2D image 140.

In step S12, after the above addition process has been carried out on the tomographic images 100, the generated 2D image 140 is stored in the 2D image memory 80. Therefore, in step S13, the display unit 84 is capable of displaying the 2D image 140 that is stored in the 2D image memory 80. In a case where controller 72 transmits the 2D image 140 to the viewer through the in-hospital network, the doctor is able to interpret and diagnose the 2D image 140 that is displayed on the viewer.

According to the fourth modification, therefore, it is possible to generate a 2D image 140, which has not captured the first marker 56 and the second marker 58, by performing on the tomographic images 100 the correcting process described in any of the above paragraphs (1) through (3). As a result, the doctor can accurately interpret and diagnose the breast 14 by observing the 2D image 140.

As described above, the first marker 56 and the second marker 58 are of a circular shape, a ring shape, a crisscross shape, or a heart shape, which is easily distinguishable from a calcified region, mass, spicula, or the like. Therefore, it is desirable for the 2D image generator 96 to distinguish the first marker 56 and the second marker 58 from a calcified region, mass, or spicula according to a known shape recognition process, before performing the addition process described above in any of paragraphs (1) through (3).

As described above, the addition process discussed in any of the above paragraphs (1) through (3) is performed on the tomographic images 100 on which the reconstructing process has been carried out, thereby generating a 2D image 140. According to the present embodiment, the 2D image generator 96 may generate the 2D image 140 by performing an addition process on the radiographic images that are stored in the projected image memory 76.

Fifth Modification

Figure 18:
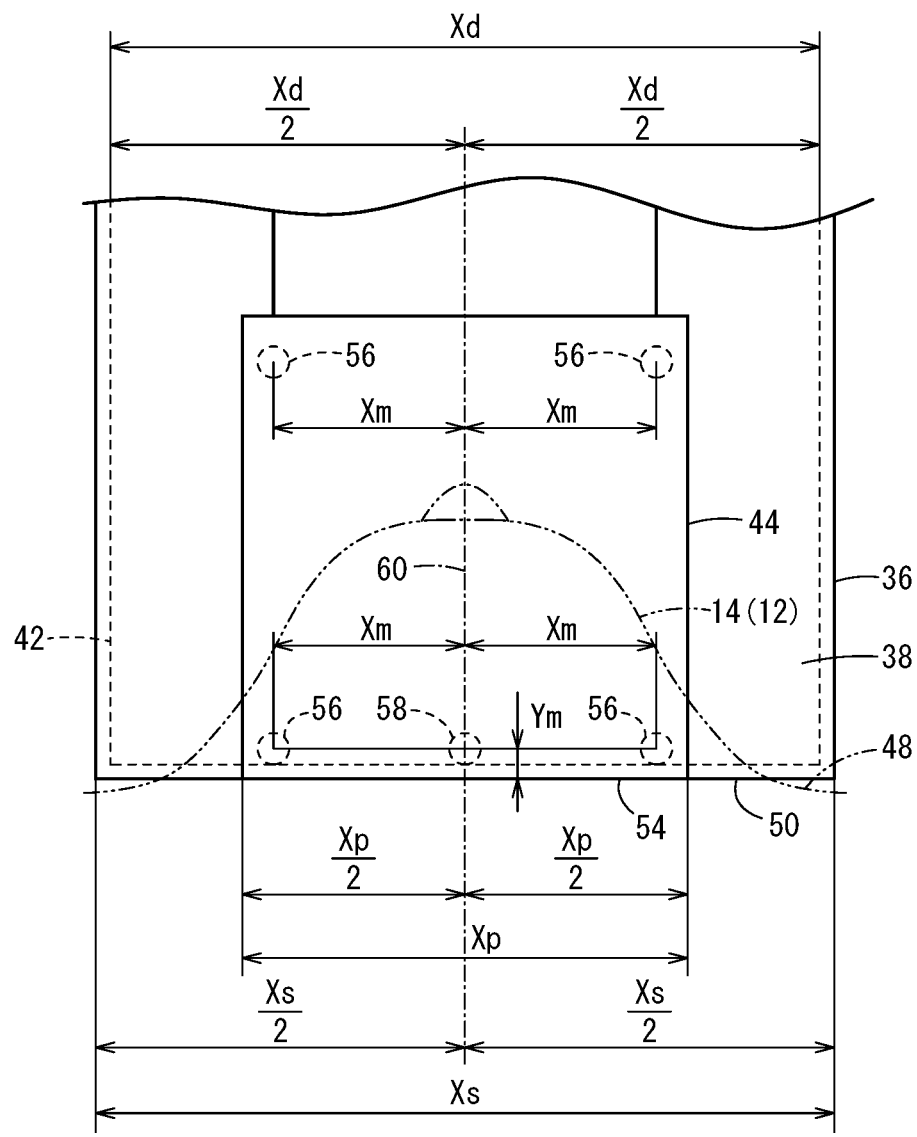
FIG. 18 is a planar view illustrating another arrangement (fifth modification) of the compression plate.

As shown in FIG. 18, the fifth modification differs from the second modification (see FIGS. 10 through 13), in that two further first markers 56 are disposed on a proximal end portion of the compression plate 44, such that the first markers 56 are provided on the four corners of the compression plate 44.

According to the fifth modification, therefore, it is possible to accurately calculate the tilt of the compression plate 44 with respect to the placement surface 38 of the image capturing table 36 (a plane along the direction of the arrow X and the direction of the arrow Y), not only in a case where the compression plate 44 is tilted laterally along the direction of the arrow X, but also in a case where the compression plate 44 is tilted along the direction of the arrow Y.

Furthermore, since the first markers 56 are provided on the four corners of the compression plate 44, it is possible to calculate the compressed thickness T at an arbitrary position in a two-dimensional plane along the direction of the arrow X and the direction of the arrow Y. Consequently, in a case where a normal image capturing process is carried out on the breast 14 after the tomosynthesis image capturing process, it is possible to accurately calculate a dose of radiation 40 to be applied in the normal image capturing process.

Sixth Modification

Figure 19:
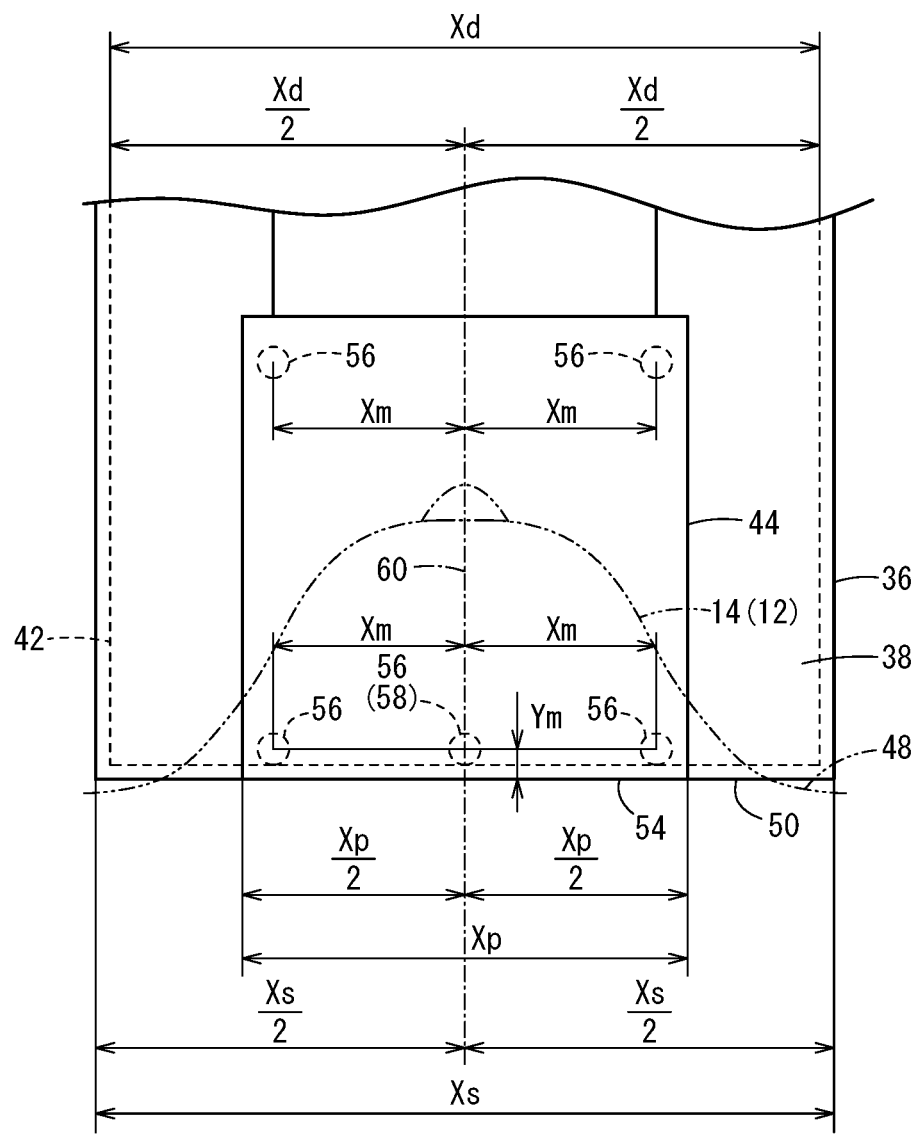
FIG. 19 is a planar view illustrating still another arrangement (sixth modification) of the compression plate.

As shown in FIG. 19, the sixth modification differs from the fifth modification (see FIG. 18), in that a further first marker 56 is disposed at a central position (the position on the vertical axis 32 and the central line 60) of the compression plate 44 proximate the side surface 54 thereof. Accordingly, the sixth modification is a combination of the arrangement of the fifth modification shown in FIG. 18 and the arrangement of the third modification shown in FIGS. 14 and 15.

Therefore, the sixth modification offers the advantages of both the fifth modification and the third modification. More specifically, according to the sixth modification, it is possible to measure the tilt of the compression plate 44 with respect to the placement surface 38 of the image capturing table 36 (a plane along the direction of the arrow X and the direction of the arrow Y) as well as the distortion of the compression plate 44.

According to the sixth embodiment, furthermore, since the compressed thickness T can be calculated at an arbitrary position in a two-dimensional plane along the direction of the arrow X and the direction of the arrow Y, in a case where a normal image capturing process is carried out on the breast 14 after the tomosynthesis image capturing process, it is possible to accurately calculate the dose of radiation 40 to be applied in the normal image capturing process.

The present invention is not limited to the embodiment described above, and changes may freely be made to the embodiment without departing from the scope of the invention.

What is claimed is:

1. A breast thickness measuring device comprising:
   a support table on which a breast of a subject is placed;
   a compression plate that is displaced toward the support table in order to compress the breast;
   a first marker provided on the compression plate on a side of a chest wall of the subject;
   a second marker provided on the support table on the side of the chest wall of the subject;
   a radiation source that applies radiation from a plurality of different angles to the breast, which has been compressed;
   a radiation detector configured to generate a plurality of image data based on radiation that has been transmitted through the breast;
   a reconstruction processor configured to reconstruct the image data in order to generate a plurality of tomographic images;
   a marker detector configured to detect tomographic images that have captured the first marker and tomographic images that have captured the second marker, from among the tomographic images;
   a marker selector configured to select a tomographic image that is focused on the first marker from among the tomographic images that have captured the first marker, and selecting a tomographic image that is focused on the second marker from among the tomographic images that have captured the second marker; and
   a thickness calculator configured to calculate a thickness of the breast, which has been compressed, based on the tomographic image that is focused on the first marker and the tomographic image that is focused on the second marker.

2. The breast thickness measuring device according to claim 1, wherein the thickness calculator calculates the thickness of the breast based on slice intervals of the tomographic images and the number of tomographic images from the tomographic image that is focused on the first marker to the tomographic image that is focused on the second marker.

3. The breast thickness measuring device according to claim 2, wherein the reconstruction processor reconstructs the image data in order to generate the tomographic images, such that the tomographic images are images sliced parallel to the support table.

4. The breast thickness measuring device according to claim 1, wherein the first marker and the second marker are disposed in superposed relation as viewed as a planar view.

5. The breast thickness measuring device according to claim 4, wherein the radiation source is supported for angular movement about a rotational shaft, and is angularly movable through a predetermined angle about a vertical axis perpendicular to the rotational shaft;
   the support table, the compression plate, and the radiation detector are disposed on the vertical axis; and
   the first marker and the second marker are disposed such that the vertical axis extends through the first marker and the second marker.

6. The breast thickness measuring device according to claim 1, wherein the first marker is disposed at one corner and another corner, along the chest wall, of the compression plate on the side of the chest wall.

7. The breast thickness measuring device according to claim 6, wherein the first marker is further disposed in a central area of the compression plate on the side of the chest wall.

8. The breast thickness measuring device according to claim 1, further comprising:
a two-dimensional image generator that generates a two-dimensional image of the breast by performing an addition process on the tomographic images;
wherein the two-dimensional image generator simply adds tomographic images, which have not captured the first marker or the second marker from among the tomographic images, in order to generate the two-dimensional image.

9. The breast thickness measuring device according to claim 1, further comprising:
a two-dimensional image generator configured to generate a two-dimensional image of the breast by performing an addition process on the tomographic images;
wherein the two-dimensional image generator:
performs a first addition process for simply adding tomographic images from among the tomographic images for image areas in which the first marker or the second marker does not exist;
performs a second addition process for simply adding, from among the tomographic images, tomographic images from which the tomographic images that have captured the first marker or the second marker are excluded, for image areas in which the first marker or the second marker exists; and
combines two new images obtained by the first addition process and the second addition process, thereby generating the two-dimensional image.

10. The breast thickness measuring device according to claim 1, further comprising:
a two-dimensional image generator that generates a two-dimensional image of the breast by performing an addition process on the tomographic images;
wherein the two-dimensional image generator:
performs a correcting process for removing the first marker or the second marker on tomographic images in which the first marker or the second marker has been captured, from among the tomographic images; and
simply adds tomographic images that have not captured the first marker or the second marker and the tomographic images on which the correcting process has been performed, thereby generating the two-dimensional image.

11. The breast thickness measuring device according to claim 1, further comprising:
an average glandular dose calculator that calculates an average glandular dose based on the thickness of the breast, which has been calculated by the thickness calculator.

12. A breast thickness measuring method comprising:
a first step of displacing a compression plate with a first marker provided thereon on the side of a chest wall of a subject, toward a support table with a second marker provided thereon on the side of the chest wall of the subject, for thereby compressing a breast of the subject that has been placed on the support table;
a second step of applying radiation from a radiation source at a plurality of different angles to the breast, which has been compressed, and generating a plurality of image data by a radiation detector based on the radiation that has been transmitted through the breast;
a third step of reconstructing the image data in order to generate a plurality of tomographic images by a reconstruction processor;
a fourth step of detecting tomographic images that have captured the first marker and tomographic images that have captured the second marker, from among the tomographic images, by a marker detector;
a fifth step of selecting a tomographic image that is focused on the first marker from among the tomographic images that have captured the first marker, and selecting a tomographic image that is focused on the second marker from among the tomographic images that have captured the second marker, by a marker selector; and
a sixth step of calculating a thickness of the breast, which has been compressed, based on the tomographic image that is focused on the first marker and the tomographic image that is focused on the second marker, by a thickness calculator.

* * * * *